United States Patent
Shone et al.

(10) Patent No.: US 8,709,428 B2
(45) Date of Patent: Apr. 29, 2014

(54) ANTIBODIES TO CLOSTRIDIUM DIFFICILE TOXINS

(75) Inventors: Clifford Shone, Salisbury (GB); John Landon, Salisbury (GB)

(73) Assignees: Health Protection Agency, Salisbury (GB); Micropharm Limited, Newcastle Emlyn (GB)

( * ) Notice: Subject to any disclaimer, the term of this patent is extended or adjusted under 35 U.S.C. 154(b) by 0 days.

(21) Appl. No.: 13/202,557

(22) PCT Filed: Feb. 19, 2010

(86) PCT No.: PCT/GB2010/050288
§ 371 (c)(1),
(2), (4) Date: Oct. 31, 2011

(87) PCT Pub. No.: WO2010/094970
PCT Pub. Date: Aug. 26, 2010

(65) Prior Publication Data
US 2012/0121607 A1  May 17, 2012

(30) Foreign Application Priority Data

Feb. 20, 2009 (GB) .................................. 0902851.5
Sep. 15, 2009 (GB) .................................. 0916153.0

(51) Int. Cl.
*A61K 39/40* (2006.01)
*A61P 31/04* (2006.01)
*C07K 16/12* (2006.01)

(52) U.S. Cl.
USPC .................................... 424/167.1; 530/389.5

(58) Field of Classification Search
None
See application file for complete search history.

(56) References Cited

U.S. PATENT DOCUMENTS

| | | | |
|---|---|---|---|
| 4,755,383 | A | 7/1988 | Fujii et al. |
| 5,601,823 | A | 2/1997 | Williams et al. |
| 5,773,000 | A | 6/1998 | Bostwick et al. |
| 6,096,310 | A | 8/2000 | Bier |
| 2004/0028705 | A1 | 2/2004 | Ballard et al. |
| 2004/0126383 | A1 | 7/2004 | Thomas, Jr. et al. |
| 2007/0071763 | A1 | 3/2007 | Burnie et al. |
| 2008/0145370 | A1 | 6/2008 | Simon |
| 2013/0004561 | A1 | 1/2013 | Shone et al. |

FOREIGN PATENT DOCUMENTS

| | | |
|---|---|---|
| CN | 101014620 | 8/2007 |
| CN | 101363867 | 2/2009 |
| WO | WO 98/59053 | 12/1998 |
| WO | WO 99/20304 | 4/1999 |
| WO | WO 99/45903 | 9/1999 |
| WO | WO 00/44402 | 8/2000 |
| WO | WO 02/43767 | 6/2002 |
| WO | WO 03/074555 | 9/2003 |
| WO | WO 2004/041857 | 5/2004 |
| WO | WO 2006/071877 | 7/2006 |
| WO | WO 2006/121422 | 11/2006 |
| WO | WO 2011/067616 | 6/2011 |

OTHER PUBLICATIONS

Greenspan et al. (Nature Biotechnology 7: 936-937, 1999).*
Barbut et al. (Journal of Medical Microbiology vol. 54, pp. 181-185).*
Lambkin, I. et al., "Targeting approaches to oral drug delivery", Expert Opinion Biol. Therapy, vol. 2, No. 1, pp. 67-73, (2002).
Bernkop-Schnurch, A., "The use of inhibitory agents to overcome the enzymatic barrier to perorally administered therapeutic peptides and proteins", Journal of Controlled Release, vol. 52, pp. 1-16, (1998).
Nguyen, V.K. et al., "Enzyme immunoassay (ELISA) for detection of *Clostridium difficile* toxin B in specimens of faeces", Journal of Medical Microbiology, vol. 31, pp. 251-257, (1990).
Warny, M. et al., "Bovine immunoglobulin concentrate—*Clostridium difficile* retains *C difficile* toxin neutralising activity after passage through the human stomach and small intestine", Gut, vol. 44, pp. 212-217, (1999).
GB Search Report dated Apr. 1, 2010 for GB application No. GB0921288.7.
International Search Report dated Mar. 18, 2011 for PCT application No. PCT/GB2010/052035.
Rummel, A. et al., "Two carbohydrate binding sites in the $H_{cc}$-domain of tetanus neurotoxin are required for toxicity", Journal of Molecular Biology, vol. 326, issue 3, pp. 835-847, (2003).
Greco, A. et al., "Carbohydrate recognition by *Clostridium difficile* toxin A", Nature Structural & Molecular Biology, vol. 13, pp. 460-461, (2006).
Ho, J.G.S. et al., "Crystal structure of receptor-binding C-terminal repeats from *Clostridium difficile* toxin A", Proceedings of the National Academy of Science, vol. 102, No. 51, pp. 18373-18378, (2005).
Guha, M.K. et al., "Purification and characterization of chymotrypsin inhibitors from marine turtle egg white", Journal of Biosciences, vol. 6, No. 2, pp. 155-163, (1984).
Greenwald, R.B. et al., "Effective drug delivery by PEGylated drug conjugates", Advanced Drug Delivery Reviews, vol. 55, issue 2, pp. 217-250, (2003).
Sundriyal, A. et al., "Expression, purification and cell cytotoxicity of actin-modifying binary toxin from *Clostridium difficile*", Protein Expression and Purification, vol. 74, issue 1, pp. 42-48, (2010).
Lineweaver, H. et al., "Identification of the trypsin inhibitor of egg white with ovomucoid", Journal of Biological Chemistry, vol. 171, No. 2, pp. 565-581, (1947).
Kakade, M.L. et al., "Determination of trypsin inhibitor activity of soy products: a collaborative analysis of an improved procedure", USDA.gov, (1974).

(Continued)

*Primary Examiner* — Robert A Zeman
(74) *Attorney, Agent, or Firm* — Evan Law Group LLC

(57) ABSTRACT

The present invention provides an antibody composition comprising ovine antibodies, for use in the prevention or treatment of *C. difficile* infection wherein the antibodies bind to a *C. difficile* toxin.

6 Claims, 6 Drawing Sheets

(56) References Cited

OTHER PUBLICATIONS

Figure 1:
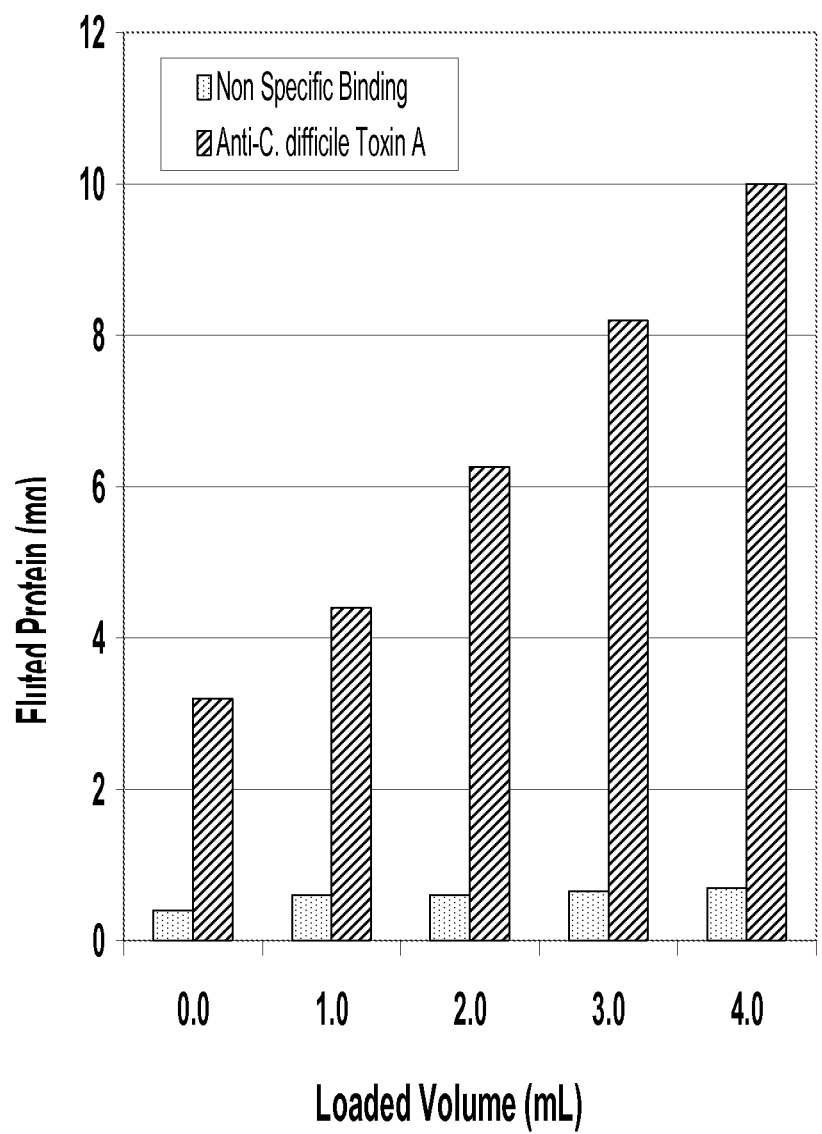

Esquisabel, A. et al., "Production of BCG alginate-PLL microcapsules by emulsification/internal gelation", Journal of Microencapsulation, vol. 14, No. 5, pp. 627-638, (1997).
Munjeri, O. et al., "In vivo behavior of hydrogel beads based on amidated pectins", Drug Delivery, vol. 5, No. 4, pp. 239-241, (1998).
Aslam, S. et al., "Treatment of *Clostridium difficile*-associated disease: old therapies and new strategies", The Lancet Infectious Diseases, vol. 5, issue 9, pp. 549-557, (2005).
Kink, J.A. et al., "Antibodies to recombinant *Clostridium difficile* toxins A and B are an effective treatment and prevent relapse of *C. difficile*-associated disease in a hamster model of infection", Infection and Immunity, vol. 66, No. 5, pp. 2018-2025, (1998).
McPherson, S. et al., "Intravenous immunoglobulin for the treatment of severe, refractory, and recurrent clostridium difficile diarrhea", Diseases of the Colon & Rectum, vol. 49, No. 5, pp. 640-645, (2006).
Baldacini, O. et al., "Comparative study of immunological properties and cytotoxic effects of *Clostridium difficile* toxin B and *Clostridium sordellii* toxin L", Toxicon, vol. 30, No. 2, pp. 129-140, (1992).
Leffler, D.A. et al., "Treatment of *Clostridium difficile*-associated disease", Gastroenterology, vol. 136, No. 6, pp. 1899-1912, (2009).
Ehrich, M. et al., "Production of clostridium difficile antitoxin", Infection and Immunity, vol. 28, No. 3, pp. 1041-1043, (1980).
Taylor, C.P. et al., "Open-label, dose escalation phase 1 study in healthy volunteers to evaluate the safety and pharmacokinetics of a human monoclonal antibody to *Clostridium difficile* toxin A", Vaccine, vol. 26, No. 26-27, pp. 3404-3409, (2008).
Young, K.W.H. et al., "The safety of whey protein concentrate derived from the milk of cows immunized against *Clostridium difficile*", Regulatory Toxicology and Pharmacology, vol. 47, pp. 317-326, (2007).
Redwan, E-R. M. et al., "Production and purification of ovine anti-tetanus antibody", Comparative Immunology Microbiology & Infectious Diseases, vol. 28, pp. 167-176, (2005).
International Search Report dated May 10, 2010 for PCT application No. PCT/GB2010/050288.
GB Search Report dated Jun. 3, 2009 for GB application No. GB0902851.5.
GB Search Report dated Jan. 15, 2010 for GB application No. GB0916153.0.
Written Opinion of the International Preliminary Examining Authority dated Mar. 8, 2011 for PCT application No. PCT/GB2010/050288.
Smith, T.F. et al., "Comparison of biosequences", Advances in Applied Mathematics, vol. 2, issue 4, pp. 482-489, (1981).
Needleman, S.B. et al., "A general method applicable to the search for similarities in the amino acid sequence of two proteins", Journal of Molecular Biology, vol. 48, issue 3, pp. 443-453, (1970).
Pearson, W.R. et al., "Improved tools for biological sequence comparison", Proceedings of the National Academy of Science, vol. 85, pp. 2444-2448, (1988).
Altschul, S.F. et al., "Basic local alignment search tool", Journal of Molecular Biology, vol. 215, issue 3, pp. 403-410, (1990).
Chothia, C. et al., "Canonical structures for the hypervariable regions of immunoglobulins}", Journal of Molecular Biology, vol. 196, pp. 901-917, (1987).
Ward, E.S. et al., "Binding activities of a repertoire of single immunoglobulin variable domains secreted from *Escherichia coli*", Nature, vol. 341, pp. 544-546, (1989).
Bird, R.E. et al., "Single-chain antigen-binding proteins", Science, vol. 242, issue 4877, pp. 423-426, (1988).
Huston, J.S. et al., "Protein engineering of antibody binding sites: Recovery of specific activity in an anti-digoxin single-chain Fv analogue produced in *Escherichia coli*", Proceedings of the National Academy of Science, vol. 85, pp. 5879-5883, (1988).
Roberts, A.K. et al., "Modification of surface hiswtiding residues abolishes the cytotoxic activity of *Clostridium difficile* toxin A", Toxicon, vol. 39, issues 2-3, pp. 325-333, (2001).
Rupnik, M. et al., "A novel tosinotyping scheme and correlation of toxinotypes with serogroups of *Clostridium difficile* isolates", Journal of Clinical Microbiology, vol. 36, No. 8, pp. 2240-2247, (1998).
Rupnik, M. et al., "Comparison of toxinotyping and PCR ribotyping of *Clostridium difficile* strains and description of novel toxinotypes", Microbiology, vol. 147, pp. 439-447, (2001).
Sambrook et al., "Molecular Cloning a Laboratory Manual", Second Edition, Cold Spring Harbor Laboratory Press, Cold spring harbor, New York (1989).
Li, M. et al., "In vitro protein refolding by chromatographic procedures", Protein Expression & Purification, vol. 33, pp. 1-10, (2004).
Yang et al., "Expression of recombinant *Clostridium difficile* toxin A and B in *Bacillus megaterium*", BMC Microbiology, vol. 8, No. 192, 13 pages, (2008).
Curd, J. et al., "The isolation of digoxin-specific antibody and its use in reversing the effects of digoxin", Proceedings of the National Academy of Science, vol. 68, No. 10, pp. 2401-2406, (1971).
Allen, G. "The affinity of binding of digoxin to ovine anti-digoxin fab (DIGIBIND™)* preparations", Biologicals, vol. 24, pp. 19-24, (1996).
Wang, X. et al., "Enzyme-linked immunosorbent assay for detection and quantitation of *Clostridium difficile* toxin A", Progress in Microbiology and Immunology, vol. 24, No. 4, pp. 7-11, (1996).
Giannasca, P.J. et al., "Serum antitoxin antibodies mediate systemic and mucosal protection from *Clostridium difficile* disease in hamsters", Infection and Immunity, vol. 67, No. 2, pp. 527-538, (1999).
Libby, J.M. et al., "Production of antitoxins to two toxins of *Clostridium difficile* and immunological comparison of the toxins by cross-neutralization studies", Infection and Immunity, vol. 35, No. 1, pp. 374-376, (1982).
van Dissel, J.T. et al., "Bovine antibody-enriched whey to aid in the prevention of a relapse of *Clostridium difficile*-associated diarrhoea: preclinical and preliminary clinical data", Journal of Medical Microbiology, vol. 54, pp. 197-205, (2005).
Kelly, C.P. et al., "Anti-*Clostridium difficile* bovine immunoglobulin concentrate inhibits cytotoxicity and enterotoxicity of *C. difficile* toxins", Antimicrobial Agents and Chemotherapy, vol. 40, No. 2, pp. 373-379, (1996).
Lyerly, D.M. et al., "Passive immunization of hamsters against disease caused by *Clostridium difficile* by use of bovine immunoglobulin G. concentrate", Infection and Immunity, vol. 59, No. 6, pp. 2215-2218, (1991).
Torres, J.F. et al., "Evaluation of formalin-inactivated *Clostridium difficile* vaccines administered by parenteral and mucosal routes of immunization in hamsters"Infection and Immunity, vol. 63, No. 12, pp. 4619-4627, (1995).
Liu, Y. et al., "Latest advances on the study of *Clostridium difficile* associated diarrhea", Chinese Journal of Infection and Chemotherapy, vol. 6, No. 4, pp. 280-283, (2006).
Translation of Peoples Republic of China Search Report obtained on Oct. 18, 2013 for CN application No. 2010/80053778.9.
Rahman, M.S. et al., "Antibody responses in buffalos immunized with *Clostridium perfringens* beta and epsilon toxoids", Vet. Med.— Czech, vol. 46, No. 9-10, pp. 241-243, (2001).
Schaeffer, T.H. et al., "Treatment of chronically digoxin-poisoned patients with a newer digoxin immune fab-a retrospective study", Journal of the American Osteopathic Association, vol. 110, No. 10, pp. 587-592, (2010).
Dart, R.C. et al., "Efficacy, safety, and use of snake antivenoms in the United States", Annals of Emergency Medicine, Toxicology/Concepts, vol. 37, No. 2, pp. 181-188, (2001).
O'Brien, J.A. et al., "The emerging infectious challenge of *Clostridium difficile*—Associated disease in Massachusetts hospitals: Clinical and economic consequences", Infection Control and Hospital Epidemiology, vol. 28, No. 11, pp. 1219-1227, (2007).
"Polyclonal antibodies" Wikipedia, found at http://en.wikipedia.org/wiki/polycional_antibodies, pp. 1-7, printed on Nov. 14, 2013.

* cited by examiner

SEQUENCE LISTING

<160> NUMBER OF SEQ ID NOS: 6

<210> SEQ ID NO 1
<211> LENGTH: 2710
<212> TYPE: PRT
<213> ORGANISM: Clostridium difficile

<400> SEQUENCE: 1

```
Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
                20                  25                  30

Tyr Asn Lys Leu Thr Thr Asn Asn Glu Asn Lys Tyr Leu Gln Leu
            35                  40                  45

Lys Lys Leu Asn Glu Ser Ile Asp Val Phe Met Asn Lys Tyr Lys Thr
50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240
```

-continued

```
Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670
```

```
Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
    690                 695                 700

Tyr Asp Phe Asn Val Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
            820                 825                 830

Ser Ile Gly Asp Tyr Ile Tyr Tyr Glu Lys Leu Glu Pro Val Lys Asn
        835                 840                 845

Ile Ile His Asn Ser Ile Asp Asp Leu Ile Asp Glu Phe Asn Leu Leu
    850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Asn Asn Ser
                885                 890                 895

Thr Tyr Ser Val Arg Phe Ile Asn Lys Ser Asn Gly Glu Ser Val Tyr
        900                 905                 910

Val Glu Thr Glu Lys Glu Ile Phe Ser Lys Tyr Ser Glu His Ile Thr
    915                 920                 925

Lys Glu Ile Ser Thr Ile Lys Asn Ser Ile Ile Thr Asp Val Asn Gly
        930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
            980                 985                 990

Ala Gln Leu Phe Ser Thr Gly Leu Asn Thr Ile Tyr Asp Ser Ile Gln
        995                 1000                1005

Leu Val Asn Leu Ile Ser Asn Ala Val Asn Asp Thr Ile Asn Val
        1010                1015                1020

Leu Pro Thr Ile Thr Glu Gly Ile Pro Ile Val Ser Thr Ile Leu
        1025                1030                1035

Asp Gly Ile Asn Leu Gly Ala Ala Ile Lys Glu Leu Leu Asp Glu
        1040                1045                1050

His Asp Pro Leu Leu Lys Lys Glu Leu Glu Ala Lys Val Gly Val
        1055                1060                1065

Leu Ala Ile Asn Met Ser Leu Ser Ile Ala Ala Thr Val Ala Ser
        1070                1075                1080

Ile Val Gly Ile Gly Ala Glu Val Thr Ile Phe Leu Leu Pro Ile
```

```
            1085                1090                1095
Ala Gly Ile Ser Ala Gly Ile Pro Ser Leu Val Asn  Asn Glu Leu
        1100                1105                1110
Ile Leu His Asp Lys Ala Thr Ser Val Val Asn Tyr  Phe Asn His
        1115                1120                1125
Leu Ser Glu Ser Lys Lys Tyr Gly Pro Leu Lys Thr  Glu Asp Asp
        1130                1135                1140
Lys Ile Leu Val Pro Ile Asp Asp Leu Val Ile Ser  Glu Ile Asp
        1145                1150                1155
Phe Asn Asn Asn Ser Ile Lys Leu Gly Thr Cys Asn  Ile Leu Ala
        1160                1165                1170
Met Glu Gly Gly Ser Gly His Thr Val Thr Gly Asn  Ile Asp His
        1175                1180                1185
Phe Phe Ser Ser Pro Ser Ile Ser Ser His Ile Pro  Ser Leu Ser
        1190                1195                1200
Ile Tyr Ser Ala Ile Gly Ile Glu Thr Glu Asn Leu  Asp Phe Ser
        1205                1210                1215
Lys Lys Ile Met Met Leu Pro Asn Ala Pro Ser Arg  Val Phe Trp
        1220                1225                1230
Trp Glu Thr Gly Ala Val Pro Gly Leu Arg Ser Leu  Glu Asn Asp
        1235                1240                1245
Gly Thr Arg Leu Leu Asp Ser Ile Arg Asp Leu Tyr  Pro Gly Lys
        1250                1255                1260
Phe Tyr Trp Arg Phe Tyr Ala Phe Phe Asp Tyr Ala  Ile Thr Thr
        1265                1270                1275
Leu Lys Pro Val Tyr Glu Asp Thr Asn Ile Lys Ile  Lys Leu Asp
        1280                1285                1290
Lys Asp Thr Arg Asn Phe Ile Met Pro Thr Ile Thr  Thr Asn Glu
        1295                1300                1305
Ile Arg Asn Lys Leu Ser Tyr Ser Phe Asp Gly Ala  Gly Gly Thr
        1310                1315                1320
Tyr Ser Leu Leu Leu Ser Ser Tyr Pro Ile Ser Thr  Asn Ile Asn
        1325                1330                1335
Leu Ser Lys Asp Asp Leu Trp Ile Phe Asn Ile Asp  Asn Glu Val
        1340                1345                1350
Arg Glu Ile Ser Ile Glu Asn Gly Thr Ile Lys Lys  Gly Lys Leu
        1355                1360                1365
Ile Lys Asp Val Leu Ser Lys Ile Asp Ile Asn Lys  Asn Lys Leu
        1370                1375                1380
Ile Ile Gly Asn Gln Thr Ile Asp Phe Ser Gly Asp  Ile Asp Asn
        1385                1390                1395
Lys Asp Arg Tyr Ile Phe Leu Thr Cys Glu Leu Asp  Asp Lys Ile
        1400                1405                1410
Ser Leu Ile Ile Glu Ile Asn Leu Val Ala Lys Ser  Tyr Ser Leu
        1415                1420                1425
Leu Leu Ser Gly Asp Lys Asn Tyr Leu Ile Ser Asn  Leu Ser Asn
        1430                1435                1440
Thr Ile Glu Lys Ile Asn Thr Leu Gly Leu Asp Ser  Lys Asn Ile
        1445                1450                1455
Ala Tyr Asn Tyr Thr Asp Glu Ser Asn Asn Lys Tyr  Phe Gly Ala
        1460                1465                1470
Ile Ser Lys Thr Ser Gln Lys Ser Ile Ile His Tyr  Lys Lys Asp
        1475                1480                1485
```

-continued

```
Ser Lys Asn Ile Leu Glu Phe Tyr Asn Asp Ser Thr Leu Glu Phe
    1490                1495                1500

Asn Ser Lys Asp Phe Ile Ala Glu Asp Ile Asn Val Phe Met Lys
    1505                1510                1515

Asp Asp Ile Asn Thr Ile Thr Gly Lys Tyr Tyr Val Asp Asn Asn
    1520                1525                1530

Thr Asp Lys Ser Ile Asp Phe Ser Ile Ser Leu Val Ser Lys Asn
    1535                1540                1545

Gln Val Lys Val Asn Gly Leu Tyr Leu Asn Glu Ser Val Tyr Ser
    1550                1555                1560

Ser Tyr Leu Asp Phe Val Lys Asn Ser Asp Gly His His Asn Thr
    1565                1570                1575

Ser Asn Phe Met Asn Leu Phe Leu Asp Asn Ile Ser Phe Trp Lys
    1580                1585                1590

Leu Phe Gly Phe Glu Asn Ile Asn Phe Val Ile Asp Lys Tyr Phe
    1595                1600                1605

Thr Leu Val Gly Lys Thr Asn Leu Gly Tyr Val Glu Phe Ile Cys
    1610                1615                1620

Asp Asn Asn Lys Asn Ile Asp Ile Tyr Phe Gly Glu Trp Lys Thr
    1625                1630                1635

Ser Ser Ser Lys Ser Thr Ile Phe Ser Gly Asn Gly Arg Asn Val
    1640                1645                1650

Val Val Glu Pro Ile Tyr Asn Pro Asp Thr Gly Glu Asp Ile Ser
    1655                1660                1665

Thr Ser Leu Asp Phe Ser Tyr Glu Pro Leu Tyr Gly Ile Asp Arg
    1670                1675                1680

Tyr Ile Asn Lys Val Leu Ile Ala Pro Asp Leu Tyr Thr Ser Leu
    1685                1690                1695

Ile Asn Ile Asn Thr Asn Tyr Tyr Ser Asn Glu Tyr Tyr Pro Glu
    1700                1705                1710

Ile Ile Val Leu Asn Pro Asn Thr Phe His Lys Lys Val Asn Ile
    1715                1720                1725

Asn Leu Asp Ser Ser Ser Phe Glu Tyr Lys Trp Ser Thr Glu Gly
    1730                1735                1740

Ser Asp Phe Ile Leu Val Arg Tyr Leu Glu Glu Ser Asn Lys Lys
    1745                1750                1755

Ile Leu Gln Lys Ile Arg Ile Lys Gly Ile Leu Ser Asn Thr Gln
    1760                1765                1770

Ser Phe Asn Lys Met Ser Ile Asp Phe Lys Asp Ile Lys Lys Leu
    1775                1780                1785

Ser Leu Gly Tyr Ile Met Ser Asn Phe Lys Ser Phe Asn Ser Glu
    1790                1795                1800

Asn Glu Leu Asp Arg Asp His Leu Gly Phe Lys Ile Ile Asp Asn
    1805                1810                1815

Lys Thr Tyr Tyr Tyr Asp Glu Asp Ser Lys Leu Val Lys Gly Leu
    1820                1825                1830

Ile Asn Ile Asn Asn Ser Leu Phe Tyr Phe Asp Pro Ile Glu Phe
    1835                1840                1845

Asn Leu Val Thr Gly Trp Gln Thr Ile Asn Gly Lys Lys Tyr Tyr
    1850                1855                1860

Phe Asp Ile Asn Thr Gly Ala Ala Leu Thr Ser Tyr Lys Ile Ile
    1865                1870                1875

Asn Gly Lys His Phe Tyr Phe Asn Asn Asp Gly Val Met Gln Leu
    1880                1885                1890
```

```
Gly Val Phe Lys Gly Pro Asp Gly Phe Glu Tyr Phe Ala Pro Ala
    1895              1900                1905
Asn Thr Gln Asn Asn Asn Ile Glu Gly Gln Ala Ile Val Tyr Gln
    1910              1915                1920
Ser Lys Phe Leu Thr Leu Asn Gly Lys Lys Tyr Tyr Phe Asp Asn
    1925              1930                1935
Asn Ser Lys Ala Val Thr Gly Trp Arg Ile Ile Asn Asn Glu Lys
    1940              1945                1950
Tyr Tyr Phe Asn Pro Asn Asn Ala Ile Ala Ala Val Gly Leu Gln
    1955              1960                1965
Val Ile Asp Asn Asn Lys Tyr Tyr Phe Asn Pro Asp Thr Ala Ile
    1970              1975                1980
Ile Ser Lys Gly Trp Gln Thr Val Asn Gly Ser Arg Tyr Tyr Phe
    1985              1990                1995
Asp Thr Asp Thr Ala Ile Ala Phe Asn Gly Tyr Lys Thr Ile Asp
    2000              2005                2010
Gly Lys His Phe Tyr Phe Asp Ser Asp Cys Val Val Lys Ile Gly
    2015              2020                2025
Val Phe Ser Thr Ser Asn Gly Phe Glu Tyr Phe Ala Pro Ala Asn
    2030              2035                2040
Thr Tyr Asn Asn Asn Ile Glu Gly Gln Ala Ile Val Tyr Gln Ser
    2045              2050                2055
Lys Phe Leu Thr Leu Asn Gly Lys Lys Tyr Tyr Phe Asp Asn Asn
    2060              2065                2070
Ser Lys Ala Val Thr Gly Leu Gln Thr Ile Asp Ser Lys Lys Tyr
    2075              2080                2085
Tyr Phe Asn Thr Asn Thr Ala Glu Ala Ala Thr Gly Trp Gln Thr
    2090              2095                2100
Ile Asp Gly Lys Lys Tyr Tyr Phe Asn Thr Asn Thr Ala Glu Ala
    2105              2110                2115
Ala Thr Gly Trp Gln Thr Ile Asp Gly Lys Lys Tyr Tyr Phe Asn
    2120              2125                2130
Thr Asn Thr Ala Ile Ala Ser Thr Gly Tyr Thr Ile Ile Asn Gly
    2135              2140                2145
Lys His Phe Tyr Phe Asn Thr Asp Gly Ile Met Gln Ile Gly Val
    2150              2155                2160
Phe Lys Gly Pro Asn Gly Phe Glu Tyr Phe Ala Pro Ala Asn Thr
    2165              2170                2175
Asp Ala Asn Asn Ile Glu Gly Gln Ala Ile Leu Tyr Gln Asn Glu
    2180              2185                2190
Phe Leu Thr Leu Asn Gly Lys Lys Tyr Tyr Phe Gly Ser Asp Ser
    2195              2200                2205
Lys Ala Val Thr Gly Trp Arg Ile Ile Asn Asn Lys Lys Tyr Tyr
    2210              2215                2220
Phe Asn Pro Asn Asn Ala Ile Ala Ala Ile His Leu Cys Thr Ile
    2225              2230                2235
Asn Asn Asp Lys Tyr Tyr Phe Ser Tyr Asp Gly Ile Leu Gln Asn
    2240              2245                2250
Gly Tyr Ile Thr Ile Glu Arg Asn Asn Phe Tyr Phe Asp Ala Asn
    2255              2260                2265
Asn Glu Ser Lys Met Val Thr Gly Val Phe Lys Gly Pro Asn Gly
    2270              2275                2280
Phe Glu Tyr Phe Ala Pro Ala Asn Thr His Asn Asn Asn Ile Glu
```

```
                    2285                2290                2295

Gly Gln Ala Ile Val Tyr Gln Asn Lys Phe Leu Thr Leu Asn Gly
2300                2305                2310

Lys Lys Tyr Tyr Phe Asp Asn Asp Ser Lys Ala Val Thr Gly Trp
2315                2320                2325

Gln Thr Ile Asp Gly Lys Lys Tyr Tyr Phe Asn Leu Asn Thr Ala
2330                2335                2340

Glu Ala Ala Thr Gly Trp Gln Thr Ile Asp Gly Lys Lys Tyr Tyr
2345                2350                2355

Phe Asn Leu Asn Thr Ala Glu Ala Ala Thr Gly Trp Gln Thr Ile
2360                2365                2370

Asp Gly Lys Lys Tyr Tyr Phe Asn Thr Asn Thr Phe Ile Ala Ser
2375                2380                2385

Thr Gly Tyr Thr Ser Ile Asn Gly Lys His Phe Tyr Phe Asn Thr
2390                2395                2400

Asp Gly Ile Met Gln Ile Gly Val Phe Lys Gly Pro Asn Gly Phe
2405                2410                2415

Glu Tyr Phe Ala Pro Ala Asn Thr Asp Ala Asn Asn Ile Glu Gly
2420                2425                2430

Gln Ala Ile Leu Tyr Gln Asn Lys Phe Leu Thr Leu Asn Gly Lys
2435                2440                2445

Lys Tyr Tyr Phe Gly Ser Asp Ser Lys Ala Val Thr Gly Leu Arg
2450                2455                2460

Thr Ile Asp Gly Lys Lys Tyr Tyr Phe Asn Thr Asn Thr Ala Val
2465                2470                2475

Ala Val Thr Gly Trp Gln Thr Ile Asn Gly Lys Lys Tyr Tyr Phe
2480                2485                2490

Asn Thr Asn Thr Ser Ile Ala Ser Thr Gly Tyr Thr Ile Ile Ser
2495                2500                2505

Gly Lys His Phe Tyr Phe Asn Thr Asp Gly Ile Met Gln Ile Gly
2510                2515                2520

Val Phe Lys Gly Pro Asp Gly Phe Glu Tyr Phe Ala Pro Ala Asn
2525                2530                2535

Thr Asp Ala Asn Asn Ile Glu Gly Gln Ala Ile Arg Tyr Gln Asn
2540                2545                2550

Arg Phe Leu Tyr Leu His Asp Asn Ile Tyr Tyr Phe Gly Asn Asn
2555                2560                2565

Ser Lys Ala Ala Thr Gly Trp Val Thr Ile Asp Gly Asn Arg Tyr
2570                2575                2580

Tyr Phe Glu Pro Asn Thr Ala Met Gly Ala Asn Gly Tyr Lys Thr
2585                2590                2595

Ile Asp Asn Lys Asn Phe Tyr Phe Arg Asn Gly Leu Pro Gln Ile
2600                2605                2610

Gly Val Phe Lys Gly Ser Asn Gly Phe Glu Tyr Phe Ala Pro Ala
2615                2620                2625

Asn Thr Asp Ala Asn Asn Ile Glu Gly Gln Ala Ile Arg Tyr Gln
2630                2635                2640

Asn Arg Phe Leu His Leu Leu Gly Lys Ile Tyr Tyr Phe Gly Asn
2645                2650                2655

Asn Ser Lys Ala Val Thr Gly Trp Gln Thr Ile Asn Gly Lys Val
2660                2665                2670

Tyr Tyr Phe Met Pro Asp Thr Ala Met Ala Ala Ala Gly Gly Leu
2675                2680                2685
```

-continued

```
Phe Glu Ile Asp Gly Val Ile Tyr Phe Phe Gly Val Asp Gly Val
    2690            2695                2700

Lys Ala Pro Gly Ile Tyr Gly
    2705            2710
```

<210> SEQ ID NO 2
<211> LENGTH: 2366
<212> TYPE: PRT
<213> ORGANISM: Clostridium difficile

<400> SEQUENCE: 2

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350
```

```
Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
        370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Asn Thr Phe Ile
                420                 425                 430

Asp Ser Ile Met Ala Glu Ala Asn Ala Asp Asn Gly Arg Phe Met Met
            435                 440                 445

Glu Leu Gly Lys Tyr Leu Arg Val Gly Phe Phe Pro Asp Val Lys Thr
        450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
        530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
                580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Asn Pro Gly
        610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
                660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
        690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Glu Ser Ile
        755                 760                 765

Ile Lys Asp Ile Ser Ser Lys Glu Tyr Ile Ser Phe Asn Pro Lys Glu
        770                 775                 780
```

-continued

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
            805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
            835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
            995                 1000                1005

Glu Leu Val Ser Thr Ala Leu Asp Glu Thr Ile Asp Leu Leu Pro
    1010                1015                1020

Thr Leu Ser Glu Gly Leu Pro Ile Ile Ala Thr Ile Ile Asp Gly
    1025                1030                1035

Val Ser Leu Gly Ala Ala Ile Lys Glu Leu Ser Glu Thr Ser Asp
    1040                1045                1050

Pro Leu Leu Arg Gln Glu Ile Glu Ala Lys Ile Gly Ile Met Ala
    1055                1060                1065

Val Asn Leu Thr Thr Ala Thr Ala Ile Ile Thr Ser Ser Leu
    1070                1075                1080

Gly Ile Ala Ser Gly Phe Ser Ile Leu Leu Val Pro Leu Ala Gly
    1085                1090                1095

Ile Ser Ala Gly Ile Pro Ser Leu Val Asn Asn Glu Leu Val Leu
    1100                1105                1110

Arg Asp Lys Ala Thr Lys Val Val Asp Tyr Phe Lys His Val Ser
    1115                1120                1125

Leu Val Glu Thr Glu Gly Val Phe Thr Leu Leu Asp Asp Lys Ile
    1130                1135                1140

Met Met Pro Gln Asp Asp Leu Val Ile Ser Glu Ile Asp Phe Asn
    1145                1150                1155

Asn Asn Ser Ile Val Leu Gly Lys Cys Glu Ile Trp Arg Met Glu
    1160                1165                1170

Gly Gly Ser Gly His Thr Val Thr Asp Asp Ile Asp His Phe Phe
    1175                1180                1185

Ser Ala Pro Ser Ile Thr Tyr Arg Glu Pro His Leu Ser Ile Tyr

```
            1190                1195                1200

Asp Val Leu Glu Val Gln Lys Glu Glu Leu Asp Leu Ser Lys Asp
        1205                1210                1215

Leu Met Val Leu Pro Asn Ala Pro Asn Arg Val Phe Ala Trp Glu
        1220                1225                1230

Thr Gly Trp Thr Pro Gly Leu Arg Ser Leu Glu Asn Asp Gly Thr
        1235                1240                1245

Lys Leu Leu Asp Arg Ile Arg Asp Asn Tyr Glu Gly Glu Phe Tyr
        1250                1255                1260

Trp Arg Tyr Phe Ala Phe Ile Ala Asp Ala Leu Ile Thr Thr Leu
        1265                1270                1275

Lys Pro Arg Tyr Glu Asp Thr Asn Ile Arg Ile Asn Leu Asp Ser
        1280                1285                1290

Asn Thr Arg Ser Phe Ile Val Pro Ile Ile Thr Thr Glu Tyr Ile
        1295                1300                1305

Arg Glu Lys Leu Ser Tyr Ser Phe Tyr Gly Ser Gly Gly Thr Tyr
        1310                1315                1320

Ala Leu Ser Leu Ser Gln Tyr Asn Met Gly Ile Asn Ile Glu Leu
        1325                1330                1335

Ser Glu Ser Asp Val Trp Ile Ile Asp Val Asp Asn Val Val Arg
        1340                1345                1350

Asp Val Thr Ile Glu Ser Asp Lys Ile Lys Lys Gly Asp Leu Ile
        1355                1360                1365

Glu Gly Ile Leu Ser Thr Leu Ser Ile Glu Glu Asn Lys Ile Ile
        1370                1375                1380

Leu Asn Ser His Glu Ile Asn Phe Ser Gly Glu Val Asn Gly Ser
        1385                1390                1395

Asn Gly Phe Val Ser Leu Thr Phe Ser Ile Leu Glu Gly Ile Asn
        1400                1405                1410

Ala Ile Ile Glu Val Asp Leu Leu Ser Lys Ser Tyr Lys Leu Leu
        1415                1420                1425

Ile Ser Gly Glu Leu Lys Ile Leu Met Leu Asn Ser Asn His Ile
        1430                1435                1440

Gln Gln Lys Ile Asp Tyr Ile Gly Phe Asn Ser Glu Leu Gln Lys
        1445                1450                1455

Asn Ile Pro Tyr Ser Phe Val Asp Ser Glu Gly Lys Glu Asn Gly
        1460                1465                1470

Phe Ile Asn Gly Ser Thr Lys Glu Gly Leu Phe Val Ser Glu Leu
        1475                1480                1485

Pro Asp Val Val Leu Ile Ser Lys Val Tyr Met Asp Asp Ser Lys
        1490                1495                1500

Pro Ser Phe Gly Tyr Tyr Ser Asn Asn Leu Lys Asp Val Lys Val
        1505                1510                1515

Ile Thr Lys Asp Asn Val Asn Ile Leu Thr Gly Tyr Tyr Leu Lys
        1520                1525                1530

Asp Asp Ile Lys Ile Ser Leu Ser Leu Thr Leu Gln Asp Glu Lys
        1535                1540                1545

Thr Ile Lys Leu Asn Ser Val His Leu Asp Glu Ser Gly Val Ala
        1550                1555                1560

Glu Ile Leu Lys Phe Met Asn Arg Lys Gly Asn Thr Asn Thr Ser
        1565                1570                1575

Asp Ser Leu Met Ser Phe Leu Glu Ser Met Asn Ile Lys Ser Ile
        1580                1585                1590
```

-continued

```
Phe Val Asn Phe Leu Gln Ser Asn Ile Lys Phe Ile Leu Asp Ala
1595                1600                1605

Asn Phe Ile Ile Ser Gly Thr Thr Ser Ile Gly Gln Phe Glu Phe
1610                1615                1620

Ile Cys Asp Glu Asn Asp Asn Ile Gln Pro Tyr Phe Ile Lys Phe
1625                1630                1635

Asn Thr Leu Glu Thr Asn Tyr Thr Leu Tyr Val Gly Asn Arg Gln
1640                1645                1650

Asn Met Ile Val Glu Pro Asn Tyr Asp Leu Asp Asp Ser Gly Asp
1655                1660                1665

Ile Ser Ser Thr Val Ile Asn Phe Ser Gln Lys Tyr Leu Tyr Gly
1670                1675                1680

Ile Asp Ser Cys Val Asn Lys Val Val Ile Ser Pro Asn Ile Tyr
1685                1690                1695

Thr Asp Glu Ile Asn Ile Thr Pro Val Tyr Glu Thr Asn Asn Thr
1700                1705                1710

Tyr Pro Glu Val Ile Val Leu Asp Ala Asn Tyr Ile Asn Glu Lys
1715                1720                1725

Ile Asn Val Asn Ile Asn Asp Leu Ser Ile Arg Tyr Val Trp Ser
1730                1735                1740

Asn Asp Gly Asn Asp Phe Ile Leu Met Ser Thr Ser Glu Glu Asn
1745                1750                1755

Lys Val Ser Gln Val Lys Ile Arg Phe Val Asn Val Phe Lys Asp
1760                1765                1770

Lys Thr Leu Ala Asn Lys Leu Ser Phe Asn Phe Ser Asp Lys Gln
1775                1780                1785

Asp Val Pro Val Ser Glu Ile Ile Leu Ser Phe Thr Pro Ser Tyr
1790                1795                1800

Tyr Glu Asp Gly Leu Ile Gly Tyr Asp Leu Gly Leu Val Ser Leu
1805                1810                1815

Tyr Asn Glu Lys Phe Tyr Ile Asn Asn Phe Gly Met Met Val Ser
1820                1825                1830

Gly Leu Ile Tyr Ile Asn Asp Ser Leu Tyr Tyr Phe Lys Pro Pro
1835                1840                1845

Val Asn Asn Leu Ile Thr Gly Phe Val Thr Val Gly Asp Asp Lys
1850                1855                1860

Tyr Tyr Phe Asn Pro Ile Asn Gly Gly Ala Ala Ser Ile Gly Glu
1865                1870                1875

Thr Ile Ile Asp Asp Lys Asn Tyr Tyr Phe Asn Gln Ser Gly Val
1880                1885                1890

Leu Gln Thr Gly Val Phe Ser Thr Glu Asp Gly Phe Lys Tyr Phe
1895                1900                1905

Ala Pro Ala Asn Thr Leu Asp Glu Asn Leu Glu Gly Glu Ala Ile
1910                1915                1920

Asp Phe Thr Gly Lys Leu Ile Ile Asp Glu Asn Ile Tyr Tyr Phe
1925                1930                1935

Asp Asp Asn Tyr Arg Gly Ala Val Glu Trp Lys Glu Leu Asp Gly
1940                1945                1950

Glu Met His Tyr Phe Ser Pro Glu Thr Gly Lys Ala Phe Lys Gly
1955                1960                1965

Leu Asn Gln Ile Gly Asp Tyr Lys Tyr Tyr Phe Asn Ser Asp Gly
1970                1975                1980

Val Met Gln Lys Gly Phe Val Ser Ile Asn Asp Asn Lys His Tyr
1985                1990                1995
```

```
Phe Asp Asp Ser Gly Val Met Lys Val Gly Tyr Thr Glu Ile Asp
    2000                2005                    2010

Gly Lys His Phe Tyr Phe Ala Glu Asn Gly Glu Met Gln Ile Gly
    2015                2020                    2025

Val Phe Asn Thr Glu Asp Gly Phe Lys Tyr Phe Ala His His Asn
    2030                2035                    2040

Glu Asp Leu Gly Asn Glu Glu Gly Glu Ile Ser Tyr Ser Gly
    2045                2050                    2055

Ile Leu Asn Phe Asn Asn Lys Ile Tyr Tyr Phe Asp Asp Ser Phe
    2060                2065                    2070

Thr Ala Val Val Gly Trp Lys Asp Leu Glu Asp Gly Ser Lys Tyr
    2075                2080                    2085

Tyr Phe Asp Glu Asp Thr Ala Glu Ala Tyr Ile Gly Leu Ser Leu
    2090                2095                    2100

Ile Asn Asp Gly Gln Tyr Tyr Phe Asn Asp Asp Gly Ile Met Gln
    2105                2110                    2115

Val Gly Phe Val Thr Ile Asn Asp Lys Val Phe Tyr Phe Ser Asp
    2120                2125                    2130

Ser Gly Ile Ile Glu Ser Gly Val Gln Asn Ile Asp Asp Asn Tyr
    2135                2140                    2145

Phe Tyr Ile Asp Asp Asn Gly Ile Val Gln Ile Gly Val Phe Asp
    2150                2155                    2160

Thr Ser Asp Gly Tyr Lys Tyr Phe Ala Pro Ala Asn Thr Val Asn
    2165                2170                    2175

Asp Asn Ile Tyr Gly Gln Ala Val Glu Tyr Ser Gly Leu Val Arg
    2180                2185                    2190

Val Gly Glu Asp Val Tyr Tyr Phe Gly Glu Thr Tyr Thr Ile Glu
    2195                2200                    2205

Thr Gly Trp Ile Tyr Asp Met Glu Asn Glu Ser Asp Lys Tyr Tyr
    2210                2215                    2220

Phe Asn Pro Glu Thr Lys Lys Ala Cys Lys Gly Ile Asn Leu Ile
    2225                2230                    2235

Asp Asp Ile Lys Tyr Tyr Phe Asp Glu Lys Gly Ile Met Arg Thr
    2240                2245                    2250

Gly Leu Ile Ser Phe Glu Asn Asn Asn Tyr Tyr Phe Asn Glu Asn
    2255                2260                    2265

Gly Glu Met Gln Phe Gly Tyr Ile Asn Ile Glu Asp Lys Met Phe
    2270                2275                    2280

Tyr Phe Gly Glu Asp Gly Val Met Gln Ile Gly Val Phe Asn Thr
    2285                2290                    2295

Pro Asp Gly Phe Lys Tyr Phe Ala His Gln Asn Thr Leu Asp Glu
    2300                2305                    2310

Asn Phe Glu Gly Glu Ser Ile Asn Tyr Thr Gly Trp Leu Asp Leu
    2315                2320                    2325

Asp Glu Lys Arg Tyr Tyr Phe Thr Asp Glu Tyr Ile Ala Ala Thr
    2330                2335                    2340

Gly Ser Val Ile Ile Asp Gly Glu Glu Tyr Tyr Phe Asp Pro Asp
    2345                2350                    2355

Thr Ala Gln Leu Val Ile Ser Glu
    2360                2365

<210> SEQ ID NO 3
<211> LENGTH: 2710
<212> TYPE: PRT
```

-continued

<213> ORGANISM: Clostridium difficile

<400> SEQUENCE: 3

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Glu Asn Lys Tyr Leu Gln Leu
        35                  40                  45

Lys Lys Leu Asn Glu Ser Ile Asp Val Phe Met Asn Lys Tyr Lys Asn
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Leu Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Pro Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala

-continued

```
                405                 410                 415
Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
            435                 440                 445

Ile Ala Pro Tyr Leu Gln Val Gly Phe Met Pro Glu Ala Arg Ser Thr
450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
            485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
            515                 520                 525

Gln Phe Glu Lys Tyr Val Arg Asp Tyr Thr Gly Gly Ser Leu Ser Glu
            530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Val Glu Ala Gly Ser
            565                 570                 575

Lys Asn Tyr Val His Tyr Ile Ile Gln Leu Gln Gly Asp Ile Ser
            580                 585                 590

Tyr Glu Ala Thr Cys Asn Leu Phe Ser Lys Asn Pro Lys Asn Ser Ile
            595                 600                 605

Ile Ile Gln Arg Asn Met Asn Glu Ser Ala Lys Ser Tyr Phe Leu Ser
610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
            645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
            675                 680                 685

Ser Pro Lys Asn Val Glu Val Asn Leu Leu Gly Cys Asn Met Phe Ser
            690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asp Ser
            725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
            755                 760                 765

Ala Ile Met Ser Asp Leu Ser Ser Lys Glu Tyr Ile Phe Phe Asp Ser
770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
            805                 810                 815

Pro Asp Thr Lys Phe Ile Leu Asn Asn Leu Lys Leu Asn Ile Glu Ser
            820                 825                 830
```

-continued

Ser Ile Gly Asp Tyr Ile Tyr Tyr Glu Lys Leu Glu Pro Val Lys Asn
    835                 840                 845

Ile Ile His Asn Ser Ile Asp Asp Leu Ile Asp Glu Phe Asn Leu Leu
850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Ser
                885                 890                 895

Thr Tyr Ser Val Arg Phe Ile Asn Lys Ser Asn Gly Glu Ser Val Tyr
            900                 905                 910

Val Glu Thr Glu Lys Glu Ile Phe Ser Lys Tyr Ser Glu His Ile Thr
        915                 920                 925

Lys Glu Ile Ser Thr Ile Lys Asn Ser Ile Ile Thr Asp Val Asn Gly
    930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
            980                 985                 990

Ala Gln Leu Phe Ser Thr Gly Leu Asn Thr Ile Tyr Asp Ser Ile Gln
        995                 1000                1005

Leu Val Asn Leu Ile Ser Asn Ala Val Asn Asp Thr Ile Asn Val
    1010                1015                1020

Leu Pro Thr Ile Thr Glu Gly Ile Pro Ile Val Ser Thr Ile Leu
    1025                1030                1035

Asp Gly Ile Asn Leu Gly Ala Ala Ile Lys Glu Leu Leu Asp Glu
    1040                1045                1050

His Asp Pro Leu Leu Lys Lys Glu Leu Glu Ala Lys Val Gly Val
    1055                1060                1065

Leu Ala Ile Asn Met Ser Leu Ser Ile Ala Ala Thr Val Ala Ser
    1070                1075                1080

Ile Val Gly Ile Gly Ala Glu Val Thr Ile Phe Leu Leu Pro Ile
    1085                1090                1095

Ala Gly Ile Ser Ala Gly Ile Pro Ser Leu Val Asn Asn Glu Leu
    1100                1105                1110

Ile Leu His Asp Lys Ala Thr Ser Val Val Asn Tyr Phe Asn His
    1115                1120                1125

Leu Ser Glu Ser Lys Glu Tyr Gly Pro Leu Lys Thr Glu Asp Asp
    1130                1135                1140

Lys Ile Leu Val Pro Ile Asp Asp Leu Val Ile Ser Glu Ile Asp
    1145                1150                1155

Phe Asn Asn Asn Ser Ile Lys Leu Gly Thr Cys Asn Ile Leu Ala
    1160                1165                1170

Met Glu Gly Gly Ser Gly His Thr Val Thr Gly Asn Ile Asp His
    1175                1180                1185

Phe Phe Ser Ser Pro Tyr Ile Ser Ser His Ile Pro Ser Leu Ser
    1190                1195                1200

Val Tyr Ser Ala Ile Gly Ile Lys Thr Glu Asn Leu Asp Phe Ser
    1205                1210                1215

Lys Lys Ile Met Met Leu Pro Asn Ala Pro Ser Arg Val Phe Trp
    1220                1225                1230

Trp Glu Thr Gly Ala Val Pro Gly Leu Arg Ser Leu Glu Asn Asn
    1235                1240                1245

```
Gly Thr Lys Leu Leu Asp Ser Ile Arg Asp Leu Tyr Pro Gly Lys
    1250            1255                1260

Phe Tyr Trp Arg Phe Tyr Ala Phe Phe Asp Tyr Ala Ile Thr Thr
    1265            1270                1275

Leu Lys Pro Val Tyr Glu Asp Thr Asn Thr Lys Ile Lys Leu Asp
    1280            1285                1290

Lys Asp Thr Arg Asn Phe Ile Met Pro Thr Ile Thr Thr Asp Glu
    1295            1300                1305

Ile Arg Asn Lys Leu Ser Tyr Ser Phe Asp Gly Ala Gly Gly Thr
    1310            1315                1320

Tyr Ser Leu Leu Leu Ser Ser Tyr Pro Ile Ser Met Asn Ile Asn
    1325            1330                1335

Leu Ser Lys Asp Asp Leu Trp Ile Phe Asn Ile Asp Asn Glu Val
    1340            1345                1350

Arg Glu Ile Ser Ile Glu Asn Gly Thr Ile Lys Lys Gly Asn Leu
    1355            1360                1365

Ile Glu Asp Val Leu Ser Lys Ile Asp Ile Asn Lys Asn Lys Leu
    1370            1375                1380

Ile Ile Gly Asn Gln Thr Ile Asp Phe Ser Gly Asp Ile Asp Asn
    1385            1390                1395

Lys Asp Arg Tyr Ile Phe Leu Thr Cys Glu Leu Asp Asp Lys Ile
    1400            1405                1410

Ser Leu Ile Ile Glu Ile Asn Leu Val Ala Lys Ser Tyr Ser Leu
    1415            1420                1425

Leu Leu Ser Gly Asp Lys Asn Tyr Leu Ile Ser Asn Leu Ser Asn
    1430            1435                1440

Thr Ile Glu Lys Ile Asn Thr Leu Gly Leu Asp Ser Lys Asn Ile
    1445            1450                1455

Ala Tyr Asn Tyr Thr Asp Glu Ser Asn Asn Lys Tyr Phe Gly Ala
    1460            1465                1470

Ile Ser Lys Thr Ser Gln Lys Ser Ile Ile His Tyr Lys Lys Asp
    1475            1480                1485

Ser Lys Asn Ile Leu Glu Phe Tyr Asn Gly Ser Thr Leu Glu Phe
    1490            1495                1500

Asn Ser Lys Asp Phe Ile Ala Glu Asp Ile Asn Val Phe Met Lys
    1505            1510                1515

Asp Asp Ile Asn Thr Ile Thr Gly Lys Tyr Tyr Val Asp Asn Asn
    1520            1525                1530

Thr Asp Lys Ser Ile Asp Phe Ser Ile Ser Leu Val Ser Lys Asn
    1535            1540                1545

Gln Val Lys Val Asn Gly Leu Tyr Leu Asn Glu Ser Val Tyr Ser
    1550            1555                1560

Ser Tyr Leu Asp Phe Val Lys Asn Ser Asp Gly His His Asn Thr
    1565            1570                1575

Ser Asn Phe Met Asn Leu Phe Leu Asn Asn Ile Ser Phe Trp Lys
    1580            1585                1590

Leu Phe Gly Phe Glu Asn Ile Asn Phe Val Ile Asp Lys Tyr Phe
    1595            1600                1605

Thr Leu Val Gly Lys Thr Asn Leu Gly Tyr Val Glu Phe Ile Cys
    1610            1615                1620

Asp Asn Asn Lys Asn Ile Asp Ile Tyr Phe Gly Glu Trp Lys Thr
    1625            1630                1635

Ser Ser Ser Lys Ser Thr Ile Phe Ser Gly Asn Gly Arg Asn Val
```

```
                1640              1645              1650

Val  Val  Glu  Pro  Ile  Tyr  Asn  Pro  Asp  Thr  Gly  Glu  Asp  Ile  Ser
1655                1660              1665

Thr  Ser  Leu  Asp  Phe  Ser  Tyr  Glu  Pro  Leu  Tyr  Gly  Ile  Asp  Arg
1670                1675              1680

Tyr  Ile  Asn  Lys  Val  Leu  Ile  Ala  Pro  Asp  Leu  Tyr  Thr  Ser  Leu
1685                1690              1695

Ile  Asn  Ile  Asn  Thr  Asn  Tyr  Tyr  Ser  Asn  Glu  Tyr  Tyr  Pro  Glu
1700                1705              1710

Ile  Ile  Val  Leu  Asn  Pro  Asn  Thr  Phe  His  Lys  Lys  Val  Asn  Ile
1715                1720              1725

Asn  Leu  Asp  Ser  Ser  Ser  Phe  Glu  Tyr  Lys  Trp  Ser  Thr  Glu  Gly
1730                1735              1740

Ser  Asp  Phe  Ile  Leu  Val  Arg  Tyr  Leu  Glu  Glu  Ser  Asn  Lys  Lys
1745                1750              1755

Ile  Leu  Gln  Lys  Ile  Arg  Ile  Lys  Gly  Ile  Leu  Ser  Asn  Thr  Gln
1760                1765              1770

Ser  Phe  Asn  Lys  Met  Ser  Ile  Asp  Phe  Lys  Asp  Ile  Lys  Lys  Leu
1775                1780              1785

Ser  Leu  Gly  Tyr  Ile  Met  Ser  Asn  Phe  Lys  Ser  Phe  Asn  Ser  Glu
1790                1795              1800

Asn  Glu  Leu  Asp  Arg  Asp  His  Leu  Gly  Phe  Lys  Ile  Ile  Asp  Asn
1805                1810              1815

Lys  Thr  Tyr  Tyr  Tyr  Asp  Glu  Asp  Ser  Lys  Leu  Val  Lys  Gly  Leu
1820                1825              1830

Ile  Asn  Ile  Asn  Asn  Ser  Leu  Phe  Tyr  Phe  Asp  Pro  Ile  Glu  Ser
1835                1840              1845

Asn  Leu  Val  Thr  Gly  Trp  Gln  Thr  Ile  Asn  Gly  Lys  Lys  Tyr  Tyr
1850                1855              1860

Phe  Asp  Ile  Asn  Thr  Gly  Ala  Ala  Ser  Thr  Ser  Tyr  Lys  Ile  Ile
1865                1870              1875

Asn  Gly  Lys  His  Phe  Tyr  Phe  Asn  Asn  Asn  Gly  Val  Met  Gln  Leu
1880                1885              1890

Gly  Val  Phe  Lys  Gly  Pro  Asp  Gly  Phe  Glu  Tyr  Phe  Ala  Pro  Ala
1895                1900              1905

Asn  Thr  Gln  Asn  Asn  Asn  Ile  Glu  Gly  Gln  Ala  Ile  Val  Tyr  Gln
1910                1915              1920

Ser  Lys  Phe  Leu  Thr  Leu  Asn  Gly  Lys  Lys  Tyr  Tyr  Phe  Asp  Asn
1925                1930              1935

Asp  Ser  Lys  Ala  Val  Thr  Gly  Trp  Arg  Ile  Ile  Asn  Asn  Glu  Lys
1940                1945              1950

Tyr  Tyr  Phe  Asn  Pro  Asn  Asn  Ala  Ile  Ala  Ala  Val  Gly  Leu  Gln
1955                1960              1965

Val  Ile  Asp  Asn  Asn  Lys  Tyr  Tyr  Phe  Asn  Pro  Asp  Thr  Ala  Ile
1970                1975              1980

Ile  Ser  Lys  Gly  Trp  Gln  Thr  Val  Asn  Gly  Ser  Arg  Tyr  Tyr  Phe
1985                1990              1995

Asp  Thr  Asp  Thr  Ala  Ile  Ala  Phe  Asn  Gly  Tyr  Lys  Thr  Ile  Asp
2000                2005              2010

Gly  Lys  His  Phe  Tyr  Phe  Asp  Ser  Asp  Cys  Val  Val  Lys  Ile  Gly
2015                2020              2025

Val  Phe  Ser  Gly  Ser  Asn  Gly  Phe  Glu  Tyr  Phe  Ala  Pro  Ala  Asn
2030                2035              2040
```

-continued

```
Thr Tyr Asn Asn Asn Ile Glu Gly Gln Ala Ile Val Tyr Gln Ser
2045                2050                2055

Lys Phe Leu Thr Leu Asn Gly Lys Lys Tyr Tyr Phe Asp Asn Asn
2060                2065                2070

Ser Lys Ala Val Thr Gly Trp Gln Thr Ile Asp Ser Lys Lys Tyr
2075                2080                2085

Tyr Phe Asn Thr Asn Thr Ala Glu Ala Ala Thr Gly Trp Gln Thr
2090                2095                2100

Ile Asp Gly Lys Lys Tyr Tyr Phe Asn Thr Asn Thr Ala Glu Ala
2105                2110                2115

Ala Thr Gly Trp Gln Thr Ile Asp Gly Lys Lys Tyr Tyr Phe Asn
2120                2125                2130

Thr Asn Thr Ser Ile Ala Ser Thr Gly Tyr Thr Ile Ile Asn Gly
2135                2140                2145

Lys Tyr Phe Tyr Phe Asn Thr Asp Gly Ile Met Gln Ile Gly Val
2150                2155                2160

Phe Lys Val Pro Asn Gly Phe Glu Tyr Phe Ala Pro Ala Asn Thr
2165                2170                2175

His Asn Asn Asn Ile Glu Gly Gln Ala Ile Leu Tyr Gln Asn Lys
2180                2185                2190

Phe Leu Thr Leu Asn Gly Lys Lys Tyr Tyr Phe Gly Ser Asp Ser
2195                2200                2205

Lys Ala Ile Thr Gly Trp Gln Thr Ile Asp Gly Lys Lys Tyr Tyr
2210                2215                2220

Phe Asn Pro Asn Asn Ala Ile Ala Ala Thr His Leu Cys Thr Ile
2225                2230                2235

Asn Asn Asp Lys Tyr Tyr Phe Ser Tyr Asp Gly Ile Leu Gln Asn
2240                2245                2250

Gly Tyr Ile Thr Ile Glu Arg Asn Asn Phe Tyr Phe Asp Ala Asn
2255                2260                2265

Asn Glu Ser Lys Met Val Thr Gly Val Phe Lys Gly Pro Asn Gly
2270                2275                2280

Phe Glu Tyr Phe Ala Pro Ala Asn Thr His Asn Asn Asn Ile Glu
2285                2290                2295

Gly Gln Ala Ile Val Tyr Gln Asn Lys Phe Leu Thr Leu Asn Gly
2300                2305                2310

Lys Lys Tyr Tyr Phe Asp Asn Asp Ser Lys Ala Val Thr Gly Trp
2315                2320                2325

Gln Thr Ile Asp Ser Lys Lys Tyr Tyr Phe Asn Leu Asn Thr Ala
2330                2335                2340

Val Ala Val Thr Gly Trp Gln Thr Ile Asp Gly Glu Lys Tyr Tyr
2345                2350                2355

Phe Asn Leu Asn Thr Ala Glu Ala Ala Thr Gly Trp Gln Thr Ile
2360                2365                2370

Asp Gly Lys Arg Tyr Tyr Phe Asn Thr Asn Thr Tyr Ile Ala Ser
2375                2380                2385

Thr Gly Tyr Thr Ile Ile Asn Gly Lys His Phe Tyr Phe Asn Thr
2390                2395                2400

Asp Gly Ile Met Gln Ile Gly Val Phe Lys Gly Pro Asp Gly Phe
2405                2410                2415

Glu Tyr Phe Ala Pro Ala Asn Thr His Asn Asn Asn Ile Glu Gly
2420                2425                2430

Gln Ala Ile Leu Tyr Gln Asn Lys Phe Leu Thr Leu Asn Gly Lys
2435                2440                2445
```

-continued

```
Lys Tyr Tyr Phe Gly Ser Asp Ser Lys Ala Val Thr Gly Leu Arg
    2450            2455                2460

Thr Ile Asp Gly Lys Lys Tyr Tyr Phe Asn Thr Asn Thr Ala Val
    2465            2470                2475

Ala Val Thr Gly Trp Gln Thr Ile Asn Gly Lys Lys Tyr Tyr Phe
    2480            2485                2490

Asn Thr Asn Thr Tyr Ile Ala Ser Thr Gly Tyr Thr Ile Ile Ser
    2495            2500                2505

Gly Lys His Phe Tyr Phe Asn Thr Asp Gly Ile Met Gln Ile Gly
    2510            2515                2520

Val Phe Lys Gly Pro Asp Gly Phe Glu Tyr Phe Ala Pro Ala Asn
    2525            2530                2535

Thr Asp Ala Asn Asn Ile Glu Gly Gln Ala Ile Arg Tyr Gln Asn
    2540            2545                2550

Arg Phe Leu Tyr Leu His Asp Asn Ile Tyr Tyr Phe Gly Asn Asp
    2555            2560                2565

Ser Lys Ala Ala Thr Gly Trp Ala Thr Ile Asp Gly Asn Arg Tyr
    2570            2575                2580

Tyr Phe Glu Pro Asn Thr Ala Met Gly Ala Asn Gly Tyr Lys Thr
    2585            2590                2595

Ile Asp Asn Lys Asn Phe Tyr Phe Arg Asn Gly Leu Pro Gln Ile
    2600            2605                2610

Gly Val Phe Lys Gly Pro Asn Gly Phe Glu Tyr Phe Ala Pro Ala
    2615            2620                2625

Asn Thr Asp Ala Asn Asn Ile Asp Gly Gln Ala Ile Arg Tyr Gln
    2630            2635                2640

Asn Arg Phe Leu His Leu Leu Gly Lys Ile Tyr Tyr Phe Gly Asn
    2645            2650                2655

Asn Ser Lys Ala Val Thr Gly Trp Gln Thr Ile Asn Ser Lys Val
    2660            2665                2670

Tyr Tyr Phe Met Pro Asp Thr Ala Met Ala Ala Ala Gly Gly Leu
    2675            2680                2685

Phe Glu Ile Asp Gly Val Ile Tyr Phe Phe Gly Val Asp Gly Val
    2690            2695                2700

Lys Ala Pro Gly Ile Tyr Gly
    2705            2710

<210> SEQ ID NO 4
<211> LENGTH: 2366
<212> TYPE: PRT
<213> ORGANISM: Clostridium difficile

<400> SEQUENCE: 4

Met Ser Leu Val Asn Arg Lys Gln Leu Glu Lys Met Ala Asn Val Arg
1               5                   10                  15

Phe Arg Val Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95
```

```
Asn Leu His Phe Val Trp Ile Gly Gly Gln Ile Asn Asp Thr Ala Ile
                100                 105                 110
Asn Tyr Ile Asn Gln Trp Lys Asp Val Asn Ser Asp Tyr Asn Val Asn
            115                 120                 125
Val Phe Tyr Asp Ser Asn Ala Phe Leu Ile Asn Thr Leu Lys Lys Thr
130                 135                 140
Ile Val Glu Ser Ala Thr Asn Asp Thr Leu Glu Ser Phe Arg Glu Asn
145                 150                 155                 160
Leu Asn Asp Pro Arg Phe Asp Tyr Asn Lys Phe Tyr Arg Lys Arg Met
                165                 170                 175
Glu Ile Ile Tyr Asp Lys Gln Lys Asn Phe Ile Asn Tyr Tyr Lys Thr
                180                 185                 190
Gln Arg Glu Glu Asn Pro Asp Leu Ile Ile Asp Asp Ile Val Lys Ile
            195                 200                 205
Tyr Leu Ser Asn Glu Tyr Ser Lys Asp Ile Asp Glu Leu Asn Ser Tyr
    210                 215                 220
Ile Glu Glu Ser Leu Asn Lys Val Thr Glu Asn Ser Gly Asn Asp Val
225                 230                 235                 240
Arg Asn Phe Glu Glu Phe Lys Gly Gly Glu Ser Phe Lys Leu Tyr Glu
                245                 250                 255
Gln Glu Leu Val Glu Arg Trp Asn Leu Ala Ala Ala Ser Asp Ile Leu
            260                 265                 270
Arg Ile Ser Ala Leu Lys Glu Val Gly Gly Val Tyr Leu Asp Val Asp
        275                 280                 285
Met Leu Pro Gly Ile Gln Pro Asp Leu Phe Glu Ser Ile Glu Lys Pro
    290                 295                 300
Ser Ser Val Thr Val Asp Phe Trp Glu Met Val Lys Leu Glu Ala Ile
305                 310                 315                 320
Met Lys Tyr Lys Glu Tyr Ile Pro Gly Tyr Thr Ser Glu His Phe Asp
                325                 330                 335
Met Leu Asp Glu Glu Val Gln Ser Ser Phe Glu Ser Val Leu Ala Ser
            340                 345                 350
Lys Ser Asp Lys Ser Glu Ile Phe Ser Ser Leu Gly Asp Met Glu Ala
        355                 360                 365
Ser Pro Leu Glu Val Lys Ile Ala Phe Asn Ser Lys Gly Ile Ile Asn
    370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Ala Phe Ile
            420                 425                 430
Asp Ser Ile Met Ala Glu Ala Asn Ala Asp Asn Gly Arg Phe Met Met
        435                 440                 445
Glu Leu Gly Lys Tyr Leu Arg Val Gly Phe Phe Pro Asp Val Lys Thr
    450                 455                 460
Thr Ile Asn Leu Ser Gly Pro Glu Ala Tyr Ala Ala Tyr Gln Asp
465                 470                 475                 480
Leu Leu Met Phe Lys Glu Gly Ser Met Asn Ile His Leu Ile Glu Ala
                485                 490                 495
Asp Leu Arg Asn Phe Glu Ile Ser Lys Thr Asn Ile Ser Gln Ser Thr
            500                 505                 510
Glu Gln Glu Met Ala Ser Leu Trp Ser Phe Asp Asp Ala Arg Ala Lys
```

```
                515                 520                 525
Ala Gln Phe Glu Glu Tyr Lys Lys Asn Tyr Phe Glu Gly Ser Leu Gly
530                 535                 540

Glu Asp Asp Asn Leu Asp Phe Ser Gln Asn Thr Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
                580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Leu Asp Val Asp Ser Leu Ser
                660                 665                 670

Thr Glu Ile Glu Thr Ala Ile Asp Leu Ala Lys Glu Asp Ile Ser Pro
                675                 680                 685

Lys Ser Ile Glu Ile Asn Leu Leu Gly Cys Asn Met Phe Ser Tyr Ser
690                 695                 700

Val Asn Val Glu Glu Thr Tyr Pro Gly Lys Leu Leu Arg Val Lys
705                 710                 715                 720

Asp Lys Val Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Ser Ile
        755                 760                 765

Ile Lys Asp Ile Ser Ser Lys Glu Tyr Ile Ser Phe Asn Pro Lys Glu
770                 775                 780

Asn Lys Ile Ile Val Lys Ser Lys Asn Leu Pro Glu Leu Ser Thr Leu
785                 790                 795                 800

Leu Gln Glu Ile Arg Asn Asn Ser Asn Ser Asp Ile Glu Leu Glu
                805                 810                 815

Glu Lys Val Met Leu Ala Glu Cys Glu Ile Asn Val Ile Ser Asn Ile
                820                 825                 830

Asp Thr Gln Val Val Glu Gly Arg Ile Glu Glu Ala Lys Ser Leu Thr
        835                 840                 845

Ser Asp Ser Ile Asn Tyr Ile Lys Asn Glu Phe Lys Leu Ile Glu Ser
850                 855                 860

Ile Ser Asp Ala Leu Tyr Asp Leu Lys Gln Gln Asn Glu Leu Glu Glu
865                 870                 875                 880

Ser His Phe Ile Ser Phe Glu Asp Ile Leu Glu Thr Asp Glu Gly Phe
        885                 890                 895

Ser Ile Arg Phe Ile Asp Lys Glu Thr Gly Glu Ser Ile Phe Val Glu
                900                 905                 910

Thr Glu Lys Ala Ile Phe Ser Glu Tyr Ala Asn His Ile Thr Glu Glu
                915                 920                 925

Ile Ser Lys Ile Lys Gly Thr Ile Phe Asp Thr Val Asn Gly Lys Leu
        930                 935                 940
```

-continued

```
Val Lys Lys Val Asn Leu Asp Ala Thr His Glu Val Asn Thr Leu Asn
945                 950                 955                 960

Ala Ala Phe Phe Ile Gln Ser Leu Ile Glu Tyr Asn Ser Ser Lys Glu
            965                 970                 975

Ser Leu Ser Asn Leu Ser Val Ala Met Lys Val Gln Val Tyr Ala Gln
        980                 985                 990

Leu Phe Ser Thr Gly Leu Asn Thr Ile Thr Asp Ala Ala Lys Val Val
    995                 1000                1005

Glu Leu Val Ser Thr Ala Leu Asp Glu Thr Ile Asp Leu Leu Pro
1010                1015                1020

Thr Leu Ser Glu Gly Leu Pro Val Ile Ala Thr Ile Ile Asp Gly
1025                1030                1035

Val Ser Leu Gly Ala Ala Ile Lys Glu Leu Ser Glu Thr Ser Asp
1040                1045                1050

Pro Leu Leu Arg Gln Glu Ile Glu Ala Lys Ile Gly Ile Met Ala
1055                1060                1065

Val Asn Leu Thr Ala Ala Thr Thr Ala Ile Ile Thr Ser Ser Leu
1070                1075                1080

Gly Ile Ala Ser Gly Phe Ser Ile Leu Leu Val Pro Leu Ala Gly
1085                1090                1095

Ile Ser Ala Gly Ile Pro Ser Leu Val Asn Asn Glu Leu Ile Leu
1100                1105                1110

Arg Asp Lys Ala Thr Lys Val Val Asp Tyr Phe Ser His Ile Ser
1115                1120                1125

Leu Ala Glu Ser Glu Gly Ala Phe Thr Ser Leu Asp Asp Lys Ile
1130                1135                1140

Met Met Pro Gln Asp Asp Leu Val Ile Ser Glu Ile Asp Phe Asn
1145                1150                1155

Asn Asn Ser Ile Thr Leu Gly Lys Cys Glu Ile Trp Arg Met Glu
1160                1165                1170

Gly Gly Ser Gly His Thr Val Thr Asp Asp Ile Asp His Phe Phe
1175                1180                1185

Ser Ala Pro Ser Ile Thr Tyr Arg Glu Pro His Leu Ser Ile Tyr
1190                1195                1200

Asp Val Leu Glu Val Gln Lys Glu Glu Leu Asp Leu Ser Lys Asp
1205                1210                1215

Leu Met Val Leu Pro Asn Ala Pro Asn Arg Val Phe Ala Trp Glu
1220                1225                1230

Thr Gly Trp Thr Pro Gly Leu Arg Ser Leu Glu Asn Asp Gly Thr
1235                1240                1245

Lys Leu Leu Asp Arg Ile Arg Asp Asn Tyr Glu Gly Glu Phe Tyr
1250                1255                1260

Trp Arg Tyr Phe Ala Phe Ile Ala Asp Ala Leu Ile Thr Thr Leu
1265                1270                1275

Lys Pro Arg Tyr Glu Asp Thr Asn Ile Arg Ile Asn Leu Asp Ser
1280                1285                1290

Asn Thr Arg Ser Phe Ile Val Pro Val Ile Thr Thr Glu Tyr Ile
1295                1300                1305

Arg Glu Lys Leu Ser Tyr Ser Phe Tyr Gly Ser Gly Gly Thr Tyr
1310                1315                1320

Ala Leu Ser Leu Ser Gln Tyr Asn Met Asn Ile Asn Ile Glu Leu
1325                1330                1335

Asn Glu Asn Asp Thr Trp Val Ile Asp Val Asp Asn Val Val Arg
1340                1345                1350
```

```
Asp Val Thr Ile Glu Ser Asp Lys Ile Lys Gly Asp Leu Ile
    1355            1360            1365

Glu Asn Ile Leu Ser Lys Leu Ser Ile Glu Asp Asn Lys Ile Ile
    1370            1375            1380

Leu Asp Asn His Glu Ile Asn Phe Ser Gly Thr Leu Asn Gly Gly
    1385            1390            1395

Asn Gly Phe Val Ser Leu Thr Phe Ser Ile Leu Glu Gly Ile Asn
    1400            1405            1410

Ala Val Ile Glu Val Asp Leu Leu Ser Lys Ser Tyr Lys Val Leu
    1415            1420            1425

Ile Ser Gly Glu Leu Lys Thr Leu Met Ala Asn Ser Asn Ser Val
    1430            1435            1440

Gln Gln Lys Ile Asp Tyr Ile Gly Leu Asn Ser Glu Leu Gln Lys
    1445            1450            1455

Asn Ile Pro Tyr Ser Phe Met Asp Asp Lys Gly Lys Glu Asn Gly
    1460            1465            1470

Phe Ile Asn Cys Ser Thr Lys Glu Gly Leu Phe Val Ser Glu Leu
    1475            1480            1485

Ser Asp Val Val Leu Ile Ser Lys Val Tyr Met Asp Asn Ser Lys
    1490            1495            1500

Pro Leu Phe Gly Tyr Cys Ser Asn Asp Leu Lys Asp Val Lys Val
    1505            1510            1515

Ile Thr Lys Asp Asp Val Ile Ile Leu Thr Gly Tyr Tyr Leu Lys
    1520            1525            1530

Asp Asp Ile Lys Ile Ser Leu Ser Phe Thr Ile Gln Asp Glu Asn
    1535            1540            1545

Thr Ile Lys Leu Asn Gly Val Tyr Leu Asp Glu Asn Gly Val Ala
    1550            1555            1560

Glu Ile Leu Lys Phe Met Asn Lys Lys Gly Ser Thr Asn Thr Ser
    1565            1570            1575

Asp Ser Leu Met Ser Phe Leu Glu Ser Met Asn Ile Lys Ser Ile
    1580            1585            1590

Phe Ile Asn Ser Leu Gln Ser Asn Thr Lys Leu Ile Leu Asp Thr
    1595            1600            1605

Asn Phe Ile Ile Ser Gly Thr Thr Ser Ile Gly Gln Phe Glu Phe
    1610            1615            1620

Ile Cys Asp Lys Asp Asn Asn Ile Gln Pro Tyr Phe Ile Lys Phe
    1625            1630            1635

Asn Thr Leu Glu Thr Lys Tyr Thr Leu Tyr Val Gly Asn Arg Gln
    1640            1645            1650

Asn Met Ile Val Glu Pro Asn Tyr Asp Leu Asp Asp Ser Gly Asp
    1655            1660            1665

Ile Ser Ser Thr Val Ile Asn Phe Ser Gln Lys Tyr Leu Tyr Gly
    1670            1675            1680

Ile Asp Ser Cys Val Asn Lys Val Ile Ile Ser Pro Asn Ile Tyr
    1685            1690            1695

Thr Asp Glu Ile Asn Ile Thr Pro Ile Tyr Glu Ala Asn Asn Thr
    1700            1705            1710

Tyr Pro Glu Val Ile Val Leu Asp Thr Asn Tyr Ile Ser Glu Lys
    1715            1720            1725

Ile Asn Ile Asn Ile Asn Asp Leu Ser Ile Arg Tyr Val Trp Ser
    1730            1735            1740

Asn Asp Gly Ser Asp Phe Ile Leu Met Ser Thr Asp Glu Glu Asn
```

-continued

```
                1745                1750                1755
Lys Val Ser Gln Val Lys Ile Arg Phe Thr Asn Val Phe Lys Gly
    1760                1765                1770
Asn Thr Ile Ser Asp Lys Ile Ser Phe Asn Phe Ser Asp Lys Gln
    1775                1780                1785
Asp Val Ser Ile Asn Lys Val Ile Ser Thr Phe Thr Pro Ser Tyr
    1790                1795                1800
Tyr Val Glu Gly Leu Leu Asn Tyr Asp Leu Gly Leu Ile Ser Leu
    1805                1810                1815
Tyr Asn Glu Lys Phe Tyr Ile Asn Asn Phe Gly Met Met Val Ser
    1820                1825                1830
Gly Leu Val Tyr Ile Asn Asp Ser Leu Tyr Tyr Phe Lys Pro Pro
    1835                1840                1845
Ile Lys Asn Leu Ile Thr Gly Phe Thr Thr Ile Gly Asp Asp Lys
    1850                1855                1860
Tyr Tyr Phe Asn Pro Asp Asn Gly Gly Ala Ala Ser Val Gly Glu
    1865                1870                1875
Thr Ile Ile Asp Gly Lys Asn Tyr Tyr Phe Ser Gln Asn Gly Val
    1880                1885                1890
Leu Gln Thr Gly Val Phe Ser Thr Glu Asp Gly Phe Lys Tyr Phe
    1895                1900                1905
Ala Pro Ala Asp Thr Leu Asp Glu Asn Leu Glu Gly Glu Ala Ile
    1910                1915                1920
Asp Phe Thr Gly Lys Leu Thr Ile Asp Glu Asn Val Tyr Tyr Phe
    1925                1930                1935
Gly Asp Asn Tyr Arg Ala Ala Ile Glu Trp Gln Thr Leu Asp Asp
    1940                1945                1950
Glu Val Tyr Tyr Phe Ser Thr Asp Thr Gly Arg Ala Phe Lys Gly
    1955                1960                1965
Leu Asn Gln Ile Gly Asp Asp Lys Phe Tyr Phe Asn Ser Asp Gly
    1970                1975                1980
Ile Met Gln Lys Gly Phe Val Asn Ile Asn Asp Lys Thr Phe Tyr
    1985                1990                1995
Phe Asp Asp Ser Gly Val Met Lys Ser Gly Tyr Thr Glu Ile Asp
    2000                2005                2010
Gly Lys Tyr Phe Tyr Phe Ala Glu Asn Gly Glu Met Gln Ile Gly
    2015                2020                2025
Val Phe Asn Thr Ala Asp Gly Phe Lys Tyr Phe Ala His His Asp
    2030                2035                2040
Glu Asp Leu Gly Asn Glu Glu Gly Glu Ala Leu Ser Tyr Ser Gly
    2045                2050                2055
Ile Leu Asn Phe Asn Asn Lys Ile Tyr Tyr Phe Asp Asp Ser Phe
    2060                2065                2070
Thr Ala Val Val Gly Trp Lys Asp Leu Glu Asp Gly Ser Lys Tyr
    2075                2080                2085
Tyr Phe Asp Glu Asp Thr Ala Glu Ala Tyr Ile Gly Ile Ser Ile
    2090                2095                2100
Ile Asn Asp Gly Lys Tyr Tyr Phe Asn Asp Ser Gly Ile Met Gln
    2105                2110                2115
Ile Gly Phe Val Thr Ile Asn Asn Glu Val Phe Tyr Phe Ser Asp
    2120                2125                2130
Ser Gly Ile Val Glu Ser Gly Met Gln Asn Ile Asp Asp Asn Tyr
    2135                2140                2145
```

-continued

```
Phe Tyr Ile Asp Glu Asn Gly Leu Val Gln Ile Gly Val Phe Asp
    2150                2155                2160
Thr Ser Asp Gly Tyr Lys Tyr Phe Ala Pro Ala Asn Thr Val Asn
    2165                2170                2175
Asp Asn Ile Tyr Gly Gln Ala Val Glu Tyr Ser Gly Leu Val Arg
    2180                2185                2190
Val Gly Glu Asp Val Tyr Tyr Phe Gly Glu Thr Tyr Thr Ile Glu
    2195                2200                2205
Thr Gly Trp Ile Tyr Asp Met Glu Asn Glu Ser Asp Lys Tyr Tyr
    2210                2215                2220
Phe Asp Pro Glu Thr Lys Lys Ala Tyr Lys Gly Ile Asn Val Ile
    2225                2230                2235
Asp Asp Ile Lys Tyr Tyr Phe Asp Glu Asn Gly Ile Met Arg Thr
    2240                2245                2250
Gly Leu Ile Thr Phe Glu Asp Asn His Tyr Tyr Phe Asn Glu Asp
    2255                2260                2265
Gly Ile Met Gln Tyr Gly Tyr Leu Asn Ile Glu Asp Lys Thr Phe
    2270                2275                2280
Tyr Phe Ser Glu Asp Gly Ile Met Gln Ile Gly Val Phe Asn Thr
    2285                2290                2295
Pro Asp Gly Phe Lys Tyr Phe Ala His Gln Asn Thr Leu Asp Glu
    2300                2305                2310
Asn Phe Glu Gly Glu Ser Ile Asn Tyr Thr Gly Trp Leu Asp Leu
    2315                2320                2325
Asp Glu Lys Arg Tyr Tyr Phe Thr Asp Glu Tyr Ile Ala Ala Thr
    2330                2335                2340
Gly Ser Val Ile Ile Asp Gly Glu Glu Tyr Tyr Phe Asp Pro Asp
    2345                2350                2355
Thr Ala Gln Leu Val Ile Ser Glu
    2360            2365

<210> SEQ ID NO 5
<211> LENGTH: 460
<212> TYPE: PRT
<213> ORGANISM: Clostridium difficile

<400> SEQUENCE: 5

Met Lys Lys Phe Arg Lys His Lys Arg Ile Ser Asn Cys Ile Ser Ile
1               5                   10                  15
Leu Leu Ile Leu Tyr Leu Thr Leu Gly Gly Leu Leu Pro Asn Asn Ile
            20                  25                  30
Tyr Ala Gln Asp Leu Gln Ser Tyr Ser Glu Lys Val Cys Asn Thr Thr
        35                  40                  45
Tyr Lys Ala Pro Ile Glu Ser Phe Leu Lys Asp Lys Glu Lys Ala Lys
    50                  55                  60
Glu Trp Glu Arg Lys Glu Ala Glu Arg Ile Glu Gln Lys Leu Glu Arg
65                  70                  75                  80
Ser Glu Lys Glu Ala Leu Glu Ser Tyr Lys Lys Asp Ser Val Glu Ile
                85                  90                  95
Ser Lys Tyr Ser Gln Thr Arg Asn Tyr Phe Tyr Asp Tyr Gln Ile Glu
            100                 105                 110
Ala Asn Ser Arg Glu Lys Glu Tyr Lys Glu Leu Arg Asn Ala Ile Ser
        115                 120                 125
Lys Asn Lys Ile Asp Lys Pro Met Tyr Val Tyr Tyr Phe Glu Ser Pro
    130                 135                 140
```

```
Glu Lys Phe Ala Phe Asn Lys Val Ile Arg Thr Glu Asn Gln Asn Glu
145                 150                 155                 160

Ile Ser Leu Glu Lys Phe Asn Glu Phe Lys Thr Ile Gln Asn Lys
            165                 170                 175

Leu Phe Lys Gln Asp Gly Phe Lys Asp Ile Ser Leu Tyr Glu Pro Gly
                180                 185                 190

Lys Gly Asp Glu Lys Pro Thr Pro Leu Leu Met His Leu Lys Leu Pro
            195                 200                 205

Arg Asn Thr Gly Met Leu Pro Tyr Thr Asn Thr Asn Asn Val Ser Thr
            210                 215                 220

Leu Ile Glu Gln Gly Tyr Ser Ile Lys Ile Asp Lys Ile Val Arg Ile
225                 230                 235                 240

Val Ile Asp Gly Lys His Tyr Ile Lys Ala Glu Ala Ser Val Val Asn
                245                 250                 255

Ser Leu Asp Phe Lys Asp Val Ser Lys Gly Asp Ser Trp Gly Lys
            260                 265                 270

Ala Asn Tyr Asn Asp Trp Ser Asn Lys Leu Thr Pro Asn Glu Leu Ala
                275                 280                 285

Asp Val Asn Asp Tyr Met Arg Gly Gly Tyr Thr Ala Ile Asn Asn Tyr
290                 295                 300

Leu Ile Ser Asn Gly Pro Val Asn Asn Pro Asn Pro Glu Leu Asp Ser
305                 310                 315                 320

Lys Ile Thr Asn Ile Glu Asn Ala Leu Lys Arg Glu Pro Ile Pro Thr
                325                 330                 335

Asn Leu Thr Val Tyr Arg Arg Ser Gly Pro Gln Glu Phe Gly Leu Thr
                340                 345                 350

Leu Thr Ser Pro Glu Tyr Asp Phe Asn Lys Leu Glu Asn Ile Asp Ala
            355                 360                 365

Phe Lys Ser Lys Trp Glu Gly Gln Ala Leu Ser Tyr Pro Asn Phe Ile
                370                 375                 380

Ser Thr Ser Ile Gly Ser Val Asn Met Ser Ala Phe Ala Lys Arg Lys
385                 390                 395                 400

Ile Val Leu Arg Ile Thr Ile Pro Lys Gly Ser Pro Gly Ala Tyr Leu
                405                 410                 415

Ser Ala Ile Pro Gly Tyr Ala Gly Glu Tyr Glu Val Leu Leu Asn His
                420                 425                 430

Gly Ser Lys Phe Lys Ile Asn Lys Ile Asp Ser Tyr Lys Asp Gly Thr
            435                 440                 445

Ile Thr Lys Leu Ile Val Asp Ala Thr Leu Ile Pro
450                 455                 460

<210> SEQ ID NO 6
<211> LENGTH: 876
<212> TYPE: PRT
<213> ORGANISM: Clostridium difficile

<400> SEQUENCE: 6

Met Lys Ile Gln Met Arg Asn Lys Lys Val Leu Ser Phe Leu Thr Leu
1               5                   10                  15

Thr Ala Ile Val Ser Gln Ala Leu Val Tyr Pro Val Tyr Ala Gln Thr
                20                  25                  30

Ser Thr Ser Asn His Ser Asn Lys Lys Glu Ile Val Asn Glu Asp
            35                  40                  45

Ile Leu Pro Asn Asn Gly Leu Met Gly Tyr Tyr Phe Ser Asp Glu His
50                  55                  60
```

-continued

```
Phe Lys Asp Leu Lys Leu Met Ala Pro Ile Lys Asp Gly Asn Leu Lys
 65                  70                  75                  80
Phe Glu Glu Lys Lys Val Asp Lys Leu Leu Asp Lys Asp Lys Ser Asp
                 85                  90                  95
Val Lys Ser Ile Arg Trp Thr Gly Arg Ile Ile Pro Ser Lys Asp Gly
            100                 105                 110
Glu Tyr Thr Leu Ser Thr Asp Arg Asp Val Leu Met Gln Val Asn
            115                 120             125
Thr Glu Ser Thr Ile Ser Asn Thr Leu Lys Val Asn Met Lys Lys Gly
            130                 135             140
Lys Glu Tyr Lys Val Arg Ile Glu Leu Gln Asp Lys Asn Leu Gly Ser
145                 150                 155                 160
Ile Asp Asn Leu Ser Ser Pro Asn Leu Tyr Trp Glu Leu Asp Gly Met
                165                 170                 175
Lys Lys Ile Ile Pro Glu Asn Leu Phe Leu Arg Asp Tyr Ser Asn
            180                 185                 190
Ile Glu Lys Asp Asp Pro Phe Ile Pro Asn Asn Asn Phe Asp Pro
            195                 200                 205
Lys Leu Met Ser Asp Trp Glu Asp Glu Asp Leu Asp Thr Asp Asn Asp
210                 215                 220
Asn Ile Pro Asp Ser Tyr Glu Arg Asn Gly Tyr Thr Ile Lys Asp Leu
225                 230                 235                 240
Ile Ala Val Lys Trp Glu Asp Ser Phe Ala Glu Gln Gly Tyr Lys Lys
                245                 250                 255
Tyr Val Ser Asn Tyr Leu Glu Ser Asn Thr Ala Gly Asp Pro Tyr Thr
                260                 265                 270
Asp Tyr Glu Lys Ala Ser Gly Ser Phe Asp Lys Ala Ile Lys Thr Glu
            275                 280                 285
Ala Arg Asp Pro Leu Val Ala Ala Tyr Pro Ile Val Gly Val Gly Met
            290                 295                 300
Glu Lys Leu Ile Ile Ser Thr Asn Glu His Ala Ser Thr Asp Gln Gly
305                 310                 315                 320
Lys Thr Val Ser Arg Ala Thr Thr Asn Ser Lys Thr Glu Ser Asn Thr
                325                 330                 335
Ala Gly Val Ser Val Asn Val Gly Tyr Gln Asn Gly Phe Thr Ala Asn
            340                 345                 350
Val Thr Thr Asn Tyr Ser His Thr Thr Asp Asn Ser Thr Ala Val Gln
            355                 360                 365
Asp Ser Asn Gly Glu Ser Trp Asn Thr Gly Leu Ser Ile Asn Lys Gly
            370                 375                 380
Glu Ser Ala Tyr Ile Asn Ala Asn Val Arg Tyr Tyr Asn Thr Gly Thr
385                 390                 395                 400
Ala Pro Met Tyr Lys Val Thr Pro Thr Thr Asn Leu Val Leu Asp Gly
                405                 410                 415
Asp Thr Leu Ser Thr Ile Lys Ala Gln Glu Asn Gln Ile Gly Asn Asn
            420                 425                 430
Leu Ser Pro Gly Asp Thr Tyr Pro Lys Lys Gly Leu Ser Pro Leu Ala
            435                 440                 445
Leu Asn Thr Met Asp Gln Phe Ser Ser Arg Leu Ile Pro Ile Asn Tyr
450                 455                 460
Asp Gln Leu Lys Lys Leu Asp Ala Gly Lys Gln Ile Lys Leu Glu Thr
465                 470                 475                 480
Thr Gln Val Ser Gly Asn Phe Gly Thr Lys Asn Ser Ser Gly Gln Ile
                485                 490                 495
```

```
Val Thr Glu Gly Asn Ser Trp Ser Asp Tyr Ile Ser Gln Ile Asp Ser
            500                 505                 510

Ile Ser Ala Ser Ile Ile Leu Asp Thr Glu Asn Glu Ser Tyr Glu Arg
            515                 520                 525

Arg Val Thr Ala Lys Asn Leu Gln Asp Pro Glu Asp Lys Thr Pro Glu
        530                 535                 540

Leu Thr Ile Gly Glu Ala Ile Glu Lys Ala Phe Gly Ala Thr Lys Lys
545                 550                 555                 560

Asp Gly Leu Leu Tyr Phe Asn Asp Ile Pro Ile Asp Glu Ser Cys Val
                565                 570                 575

Glu Leu Ile Phe Asp Asp Asn Thr Ala Asn Lys Ile Lys Asp Ser Leu
            580                 585                 590

Lys Thr Leu Ser Asp Lys Lys Ile Tyr Asn Val Lys Leu Glu Arg Gly
            595                 600                 605

Met Asn Ile Leu Ile Lys Thr Pro Thr Tyr Phe Thr Asn Phe Asp Asp
            610                 615                 620

Tyr Asn Asn Tyr Pro Ser Thr Trp Ser Asn Val Asn Thr Thr Asn Gln
625                 630                 635                 640

Asp Gly Leu Gln Gly Ser Ala Asn Lys Leu Asn Gly Glu Thr Lys Ile
                645                 650                 655

Lys Ile Pro Met Ser Glu Leu Lys Pro Tyr Lys Arg Tyr Val Phe Ser
                660                 665                 670

Gly Tyr Ser Lys Asp Pro Leu Thr Ser Asn Ser Ile Ile Val Lys Ile
                675                 680                 685

Lys Ala Lys Glu Glu Lys Thr Asp Tyr Leu Val Pro Glu Gln Gly Tyr
            690                 695                 700

Thr Lys Phe Ser Tyr Glu Phe Glu Thr Glu Lys Asp Ser Ser Asn
705                 710                 715                 720

Ile Glu Ile Thr Leu Ile Gly Ser Gly Thr Thr Tyr Leu Asp Asn Leu
                725                 730                 735

Ser Ile Thr Glu Leu Asn Ser Thr Pro Glu Ile Leu Asp Glu Pro Glu
            740                 745                 750

Val Lys Ile Pro Thr Asp Gln Glu Ile Met Asp Ala His Lys Ile Tyr
            755                 760                 765

Phe Ala Asp Leu Asn Phe Asn Pro Ser Thr Gly Asn Thr Tyr Ile Asn
        770                 775                 780

Gly Met Tyr Phe Ala Pro Thr Gln Thr Asn Lys Glu Ala Leu Asp Tyr
785                 790                 795                 800

Ile Gln Lys Tyr Arg Val Glu Ala Thr Leu Gln Tyr Ser Gly Phe Lys
                805                 810                 815

Asp Ile Gly Thr Lys Asp Lys Glu Met Arg Asn Tyr Leu Gly Asp Pro
            820                 825                 830

Asn Gln Pro Lys Thr Asn Tyr Val Asn Leu Arg Ser Tyr Phe Thr Gly
            835                 840                 845

Gly Glu Asn Ile Met Thr Tyr Lys Lys Leu Arg Ile Tyr Ala Ile Thr
            850                 855                 860

Pro Asp Asp Arg Glu Leu Leu Val Leu Ser Val Asp
865                 870                 875
```

ANTIBODIES TO *CLOSTRIDIUM DIFFICILE* TOXINS

SEQUENCE LISTING INCORPORATION BY REFERENCE

A sequence listing in an ASCII text file, having the name "MSQ07-024-US_SEQUENCE_LISTING_FOR_N-MP.txt", created on 9 Sep. 2011, and having a size of 99 kb, is hereby incorporated by reference in its entirety.

The present invention relates to ovine antibodies and their use in the prevention or treatment of *Clostridium difficile* infection (CDI).

*Clostridium difficile* infection (CDI) is now a major problem in hospitals worldwide. The bacterium causes nosocomial, antibiotic-associated disease which manifests itself in several forms ranging from mild self-limiting diarrhoea to potentially life-threatening, severe colitis. Elderly patients are most at risk from these potentially life-threatening diseases and incidents of CDI have increased dramatically over the last 10 years. In 2007 in the UK there were over 50,000 cases of CDI with over 8,000 associated deaths. CDI costs the NHS >£500 M per annum.

The various strains of *C. difficile* may be classified by a number of methods. One of the most commonly used is polymerase chain reaction (PCR) ribotyping in which PCR is used to amplify the 16S-23S rRNA gene intergenic spacer region of *C. difficile*. Reaction products from this provide characteristic band patterns identifying the bacterial ribotype of isolates. Toxinotyping is another typing method in which the restriction patterns derived from DNA coding for the *C. difficile* toxins are used to identify strain toxinotype. The differences in restriction patterns observed between toxin genes of difference strains are also indicative of sequence variation within the *C. difficile* toxin family. Toxin B shows sequence variation in some regions. For example, there's an approximate 13% sequence difference with the C-terminal 60 kDa region of toxinotype 0 Toxin B compared to the same region in toxinotype III. Although such sequence differences are relatively small, they can be extremely important with respect to the antigenic properties of the molecule and can have a profound impact on antibody binding and hence the toxin-neutralisation properties by antibodies.

Strains of *C. difficile* produce a variety of virulence factors, notable among which are several protein toxins: Toxin A, Toxin B and, in some strains, a binary toxin which is similar to *Clostridium perfringens* iota toxin. Toxin A is a large protein cytotoxin/enterotoxin which plays a role in the pathology of infection and may influence in the gut colonisation process. Outbreaks of CDI have been reported with Toxin A-negative/Toxin B-positive strains which suggests that Toxin B is also capable of playing a key role in the disease pathology. Both Toxins A and B exert their mechanisms of action via multi-step mechanisms which include binding to receptors on the cell surface, internalisation followed by translocation and release of the effector domain into the cell cytosol and finally intracellular action. For both Toxins A and B this involves the inactivation of small GTPases of the Rho family. For this inactivation, each toxin catalyses the transfer of a glucose moiety (from UDP-glucose) onto an amino residue of the Rho protein. Both Toxins A and B also contain a second enzyme activity in the form of a cysteine protease which appears to play a role in the release of the effector domain into the cytosol after translocation. The *C. difficile* binary toxin works in a different way, modifying cell actin by a mechanism which involves the transfer of an ADP-ribose moiety from NAD onto its target protein.

Treatment of *C. difficile* infection currently relies on antibiotics of which metronidazole and vancomycin constitute the treatment of choice. However, these antibiotics are not effective in all cases and 20-30% of patients suffer relapse of the disease. Of major concern is the appearance in the UK of more virulent strains which were first identified in Canada in 2002. These strains, which belong to PCR ribotype 027, toxinotype III, cause CDI with a directly attributable mortality more than 3-fold that observed previously.

New therapeutics are therefore required especially urgently since the efficacy of current antibiotics appears to be decreasing.

Accordingly, there is a need in the art for new therapies/therapeutics capable of specifically addressing *C. difficile* infection (CDI). This need is addressed by the present invention, which solves one or more of the above-mentioned problems.

In more detail, a first aspect of the present invention provides ovine antibodies, for use in the prevention or treatment of CDI. In another aspect, the invention provides an antibody composition comprising the ovine antibodies, for use in the prevention or treatment of CDI. In one embodiment, the ovine antibodies are polyclonal antibodies.

In use, the antibodies of the invention bind to a *C. difficile* toxin or a fragment thereof, preferably neutralising the biological activity of the toxin or fragment thereof. Accordingly, the antibodies of the present invention are capable of preventing or treating CDI, and preferably also preventing a relapse in a patient.

The antibodies of the present invention provide a distinct advantage over other therapeutics in that they are able to inhibit the biological action of one or more of the toxins of *C. difficile*, whilst having a low immunogenic effect on a patient. Moreover, the antibodies of the present invention can be produced in high titres. Thus, the ovine antibodies can be readily obtained and can protect and/or the patient against the pathological effects produced by *C. difficile* with minimal side-effects. The antibodies of the present invention may also be utilised in the development of a vaccine for passive immunization against CDI.

The principal targets of the present invention are *C. difficile* toxins or fragments thereof. Suitable *C. difficile* toxins, to which the antibodies of the invention may bind to and/or neutralise, include any *C. difficile* toxins that cause or are associated with CDI or a symptom thereof. In a further embodiment, the antibodies of the invention bind to and/or neutralise at least one type of *C. difficile* toxin selected from the following: *C. difficile* Toxin A or a fragment thereof, *C. difficile* Toxin B or a fragment thereof, and *C. difficile* Binary Toxin or a fragment thereof.

Thus, in one embodiment, the antibody composition of the present invention comprises ovine antibodies that bind to and/or neutralise *C. difficile* Toxin A (or a fragment thereof). In another embodiment, the antibody composition of the present invention comprises ovine antibodies that bind to and/or neutralise *C. difficile* Toxin B (or a fragment thereof). In yet another embodiment, the antibody composition of the present invention comprises ovine antibodies that bind to and/or neutralise *C. difficile* Binary Toxin (or a fragment thereof).

In another embodiment, the antibody composition of the present invention comprises ovine antibodies that bind to and/or neutralise *C. difficile* Toxin A (or a fragment thereof) and to *C. difficile* Toxin B (or a fragment thereof). In another embodiment, the antibody composition of the present invention comprises ovine antibodies that bind to and/or neutralise *C. difficile* Toxin A (or a fragment thereof) and to *C. difficile*

Binary Toxin (or a fragment thereof). In yet another embodiment, the antibody composition of the present invention comprises ovine antibodies that bind to and/or neutralise *C. difficile* Toxin B (or a fragment thereof) and to *C. difficile* Binary Toxin (or a fragment thereof).

The antibody composition of the present invention may also comprise ovine antibodies that bind to and/or neutralise *C. difficile* Toxin A (or a fragment thereof), to *C. difficile* Toxin B (or a fragment thereof) and to *C. difficile* Binary Toxin (or a fragment thereof).

In one embodiment, the antibody composition comprises a first antibody that binds to and/or neutralises *C. difficile* Toxin A (or a fragment thereof), and a second antibody selected from an antibody that binds to and/or neutralises *C. difficile* Toxin B (or a fragment thereof) or an antibody that bind to and/or neutralise *C. difficile* Binary Toxin (or a fragment thereof). In this embodiment, the second antibody may bind to and/or neutralise *C. difficile* Toxin B (or a fragment thereof), and the composition optionally includes a third antibody that binds to and/or neutralises *C. difficile* Binary Toxin (or a fragment thereof).

In another embodiment, the antibody composition comprises a first antibody that binds to and/or neutralises *C. difficile* Toxin B (or a fragment thereof), and a second antibody selected from an antibody that binds to and/or neutralises *C. difficile* Toxin A (or a fragment thereof) or an antibody that bind to and/or neutralise *C. difficile* Binary Toxin (or a fragment thereof). In this embodiment, the second antibody may bind to and/or neutralise *C. difficile* Toxin A (or a fragment thereof), and the composition optionally includes a third antibody that binds to and/or neutralises *C. difficile* Binary Toxin (or a fragment thereof).

In another embodiment, the antibody composition comprises a first antibody that binds to and/or neutralises *C. difficile* Binary Toxin (or a fragment thereof), and a second antibody selected from an antibody that binds to and/or neutralises *C. difficile* Toxin A (or a fragment thereof) or an antibody that bind to and/or neutralise *C. difficile* Toxin B (or a fragment thereof). In this embodiment, the second antibody may bind to and/or neutralise *C. difficile* Toxin A (or a fragment thereof), and the composition optionally includes a third antibody that binds to and/or neutralises *C. difficile* Toxin B (or a fragment thereof). Alternatively, the second antibody may bind to and/or neutralise *C. difficile* Toxin B (or a fragment thereof), and the composition optionally includes a third antibody that binds to and/or neutralises *C. difficile* Toxin A (or a fragment thereof).

An antibody of the invention may (specifically) bind and/or neutralise one of *C. difficile* Toxin A (or a fragment thereof) or *C. difficile* Toxin B (or a fragment thereof) or *C. difficile* Binary Toxin (or a fragment thereof). Alternatively, an antibody of the invention may bind two or more of *C. difficile* Toxin A (or a fragment thereof) or *C. difficile* Toxin B (or a fragment thereof) or *C. difficile* Binary Toxin (or a fragment thereof). When an antibody binds and/or neutralises two or more Toxin types, said antibody preferably binds and/or neutralises *C. difficile* Toxin B (or a fragment thereof) plus one or both of *C. difficile* Toxin A (or a fragment thereof) and/or *C. difficile* Binary Toxin (or a fragment thereof).

The antibodies of the present invention interact with specific epitopes of the toxin. For example, an antibody can bind an epitope in the N-terminal domain (e.g. between amino acids 1-957) or the mid-region domains (e.g. between amino acids 958-1831) or the C-terminal repeat domains (e.g. between amino acids 1832-2710) of *C. difficile* Toxin A. For example, the antibody may bind to an epitope within amino acids 1832-2710 of *C. difficile* Toxin A. Similarly an antibody can bind an epitope in the N-terminal domain (e.g. between amino acids 1-955) or the mid-region domains (e.g. between amino acids 956-1831) or the C-terminal repeat domains (e.g. between amino acids 1832-2366) of Toxin B. For example, an antibody may bind to an epitope within amino acids 1832-2366 of Toxin B. In the case of the binary toxin antibodies may bind to the catalytic domain (Fragment A) or the receptor binding domain, which resides in the C-terminal portion of Fragment B (approx residues 400-870); and/or to the N-terminal half of Fragment B (approx residues 1-400), which is involved in the binding and translocation of Fragment A into the cell.

In one embodiment, the *C. difficile* toxin is selected from one of toxinotypes 0 to XV. Preferred toxinotypes (plus example Ribotypes and Strains) are listed in Table 1 immediately below. The listed toxinotypes are purely illustrative and are not intended to be limiting to the present invention.

TABLE 1

| Toxinotype | Example Ribotypes | Example Strains | Reference |
|---|---|---|---|
| 0 | 001, 106 | VPI10463 | Rupnik et al. |
| I | 003, 012, 102 | EX623 | (1998) |
| II | 103 | AC008 | J. Clinical |
| III | 027, 034, 075, 080 | R20291, QCD-32g58 | Microbiol. 36: 2240-2247 |
| IV | 023, 034, 075, 080 | 55767 | |
| V | 066, 078 | SE881 | |
| VI | 045, 063, 066 | 51377 | |
| VII | 063 | 57267 | |
| VIII | 017, 047 | 1470 | |
| IX | 019 | 51680 | |
| X | 036 | 8864 | |
| XI | 033 | IS58, R11402 | Rupnik et al. |
| XII | 056 | IS25 | (2001) |
| XIII | 070 | R9367 | Microbiology |
| XIV | 111 | R10870 | 147: 439-447 |
| XV | 122 | R9385 | |

Different antibodies of the present invention may bind to and/or neutralise the same or different strains of *C. difficile* toxin. For example, the antibodies may bind to and/or neutralise one or more of the following: *C. difficile* Toxin A-Toxinotype 0; *C. difficile* Toxin B-Toxinotype 0; *C. difficile* Toxin A-Toxinotype III; *C. difficile* Toxin B-Toxinotype III; *C. difficile* Toxin A-Toxinotype V; and/or *C. difficile* Toxin B-Toxinotype V. Preferably, a mixture of antibodies is employed, which bind to and/or neutralise Toxins A and B from all of these Toxinotypes. An antibody of the present invention may bind to an epitope in the N-terminal domain, the mid-region domain, and/or the C-terminal repeat domain of said strains of *C. difficile* Toxin A and/or *C. difficile* Toxin B.

In certain embodiments, the antibodies of the present invention may bind to and/or neutralise at least one *C. difficile* toxin comprising an amino acid sequence at least 80%, 85%, 90%, 95%, 98%, 99%, or more identical to SEQ ID NOs: 1-6, or a fragment thereof.

The invention also embraces a corresponding method for prevention or treatment of CDI, said method comprising administering the antibody composition of the present invention to a patient. The patient can be infected with *C. difficile*, or have a symptom of *C. difficile* (e.g. mild self-limiting diarrhoea, abdomen pain, fever and loss of appetite to life-threatening conditions such as pseudomembranous colitis and cytotoxic megacolon) or have a predisposition towards *C. difficile* infection (e.g. undergoing treatment with antibiotics, having experienced *C. difficile* and at risk of relapse, or exposed to a second individual who has shown the clinical symptoms associated with *C. difficile* infection). The present invention thereby provides an effective means for preventing or treating CDI.

In one embodiment, said method of treating CDI comprises administering the antibody composition of the present invention to a patient infected with *C. difficile*, or suffering from the symptoms of CDI. This can be accomplished using a therapeutically effective amount of the antibodies. Such administration may be effected by repeated administrations of antibody compositions of the present invention, for a prolonged period of time. The antibody components of said compositions may be the same or different (in terms of their toxinotype specificity and/or targeted binding region or epitope on a *C. difficile* Toxin), and administration can be concurrent or sequential, and can be effected in any order.

In another embodiment, said method of preventing CDI comprises administering the antibody composition of the present invention to a patient to provide passive immunity against CDI. This can be accomplished using a prophylactically effective amount of the antibodies prior to the onset or in the very early stages of CDI. Such administration may be effected by repeated administrations of antibody compositions of the present invention, for a prolonged period of time. The antibody components of said compositions may be the same or different (in terms of their toxinotype specificity and/or targeted binding region or epitope on a *C. difficile* Toxin), and administration can be concurrent or sequential, and can be effected in any order.

Antibody Preparation

The ovine antibodies are antibodies which have been raised in a sheep. Thus, the present invention includes a method of producing ovine antibodies for use in the antibody composition of the invention, said method generally involving (i) administering an immunogen comprising a *C. difficile* toxin or a fragment thereof to a sheep, (ii) allowing sufficient time for the generation of antibodies in the sheep, and (iii) obtaining the antibodies from the sheep. As used herein, sheep comprise any species that fall within the *Ovis* genus (e.g. *Ovis ammon, Ovis orientalis aries, Ovis orientalis orientalis, Ovis orientalis vignei, Ovis Canadensis, Ovis dalli, Ovis nivicola*).

The present invention also includes a method of producing ovine antibodies for use in the antibody composition of the invention, wherein the ovine antibodies are elicited by a sheep in response to an immunogen comprising a *C. difficile* toxin or a fragment thereof (preferably a fragment that possesses antigenic cross-reactivity with the full-length natural Toxin and/or retains the toxin or toxin-like activity of the full-length natural Toxin).

The antibody may be obtained from the sheep serum. Thus, the procedures generate sheep antisera containing antibodies capable of binding and neutralising *C. difficile* toxins. In a further embodiment, the antibodies are isolated and/or purified. Thus, another aspect of the present invention involves purifying the antibodies from sheep antiserum.

In one embodiment, the immunogen used to generate the antibodies of the present invention is a *C. difficile* toxin or a fragment thereof, which has optionally been purified. Suitable *C. difficile* toxins include any *C. difficile* toxins that cause or are associated with CDI or a symptom thereof. In a further embodiment, the toxin is selected from at least one of the following toxins: *C. difficile* Toxin A or a fragment thereof, *C. difficile* Toxin B or a fragment thereof and *C. difficile* Binary Toxin or a fragment thereof. The *C. difficile* toxin may also be a toxin selected from one of the toxinotypes 0 to XV as defined hereinbefore.

Production of a purified *C. difficile* toxin is exemplified in the Examples. In certain embodiments, the immunogen is a *C. difficile* toxin variant. In another embodiment the immunogen comprises an amino acid sequence at least 80%, 85%, 90%, 95%, 98%, 99%, or more identical to SEQ ID NOs: 1-6, or a fragment thereof.

The immunogen used to generate the antibodies of the present invention may also be partially or completely inactivated, i.e. have reduced toxicity. Examples of modification include: chemical treatment (e.g. treatment with UDP-dialdehyde, formaldehyde, glutaraldehyde, peroxide, or oxygen) and recombinant methods (e.g. deletions or mutations in the toxin). For example, the immunogen may be a *C. difficile* toxoid or a fragment thereof derived from the native toxin by treatment with formaldehyde. Alternatively, a recombinant toxoid may be generated by selectively inactivating the active site motif by site-directed mutagenesis. An example of site directed mutagenesis to reduce or ablate the toxin effects of Toxins A and B is modification of the DXD motif in the N-terminal domain of the toxin. The aspartates and/or other residues may be mutated to e.g. alanine in order to reduce the biological activity of either Toxin A and B. For example, for Toxin A one of more of the following amino acids may be mutated: Asp 269, Asp285, Asp 287, Asn383, Trp519, Tyr283, Arg272. For Toxin B one of more of the following amino acids may be mutated: Asp270, Asp286, Asp 288, Asn384, Trp520, Tyr284, Arg273.

Antigens may be formulated with an adjuvant. Suitable adjuvants may include alum (aluminium phosphate or aluminium hydroxide), which is used widely in humans, and other adjuvants such as saponin and its purified component Quil A, Freund's complete adjuvant, RIBBI adjuvant, and other adjuvants used in research and veterinary applications.

The *C. difficile* toxins or toxoids may be used as immunogens separately or in combination, either concurrently or sequentially, in order to produce antibodies specific for individual *C. difficile* toxins or combinations. For example, two or more toxins or toxoids may be mixed together and used as a single immunogen. Alternatively a *C. difficile* toxin (e.g. *C. difficile* Toxin A) may be used separately as a first immunogen on a first sheep or goat, and another *C. difficile* toxin (e.g. *C. difficile* Toxin B) may be used separately on a second sheep or goat. The antibodies produced by separate immunisation may be combined to yield an antibody composition directed against *C. difficile* toxins.

The method comprises all modes of immunisation, including subcutaneous, intramuscular, intraperitoneal, and intravenous. The invention also contemplates a wide variety of immunisation schedules. In one embodiment, a sheep or goat is administered toxin(s) on day zero and subsequently receives toxin(s) at intervals thereafter. It will be appreciated that the interval range and dosage range required depends on the precise nature of the immunogen, the route of administration, the nature of the formulation, and the judgement of the attending person. Variations in these dosage levels can be adjusted using standard empirical routines for optimisation. Similarly, it is not intended that the present invention be limited to any particular schedule for collecting antibody. The preferred collection time is someday after day 56. Levels of the specific antibody, i.e. that which binds to the immunogen, should represent at least 3 g per liter of serum.

The antibodies of the invention may be modified as necessary after collection, so that, in certain instances, they are less immunogenic in the patient to whom they are administered. For example, if the patient is a human, the antibodies may be despeciated by methods well known in the art. One example as to how an antibody can be made less immunogenic is to prepare the $(Fab)_2$ fragment. The antibodies of the invention may be used to produce such antibody fragments for which various techniques have been developed. For example, the fragments may be derived by proteolytic digestion of intact antibodies. Other techniques for their production will be apparent to the skilled practitioner.

Antibody Delivery

In use, the present invention employs a pharmaceutical composition, comprising the antibody composition of the present invention in a form suitable for parenteral, usually intravenous administration. The purified intact antibodies, or their fragments, are formulated for such delivery. For example, antibody, or its fragment, at a concentration between 5-50 or 15-50 or 25-50 g/liter may be formulated in buffer. Examples of suitable buffer components include physiological salts such as sodium citrate and/or citric acid. Preferred buffers contain 100-200 or 125-175 or approximately 150 (eg. 153) mM physiological salts such as sodium chloride. Preferred buffers maintain the pharmaceutical composition at a pH that is close to the physiological pH of the patient—for example, at a pH of 5.5-6.4, or at a pH of 5.6-6.3, or at a pH of 5.7-6.2, or at a pH of 5.8-6.2. The antibody-containing compositions of the present invention preferably exclude adjuvant(s) as it is undesirable to stimulate an immune response against said antibodies in the patient.

Antibodies of the invention may be formulated for, but not limited to intramuscular, subcutaneous or intravenous delivery. Compositions suitable for intramuscular, subcutaneous or intravenous injection include sterile aqueous solutions. Such aqueous solutions should be suitably buffered if necessary and the liquid diluent first rendered isotonic with sufficient saline or glucose. The antibody compositions of the present invention are not oral formulations, and this mode of administration is not employed. In this regard, a key problem with oral delivery is ensuring that sufficient antibody reaches the colon where it is required. Factors which prevent antibody reaching the gut include the proteolytic enzymes present in the digestive secretions, which degrade the antibody molecule and also in some instances the effect of CDI itself which can cause paralytic ileus and other complications that prevent movement of fluids down the alimentary canal.

Compositions suitable for injection may be in the form of solutions, suspensions or dry powders which are dissolved or suspended in a suitable vehicle prior to use.

In preparing solutions of the antibodies or their fragments can be dissolved in the vehicle, the solution being made isotonic if necessary by addition of sodium chloride and sterilised by filtration through a sterile filter using aseptic techniques before filling into suitable sterile vials or ampoules and sealing. Advantageously additives such as buffering, solubilising, stabilising, preservative or bactericidal or suspending and/or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

The dosage ranges for administration of the antibodies of the present invention are those to produce the desired therapeutic effect. It will be appreciated that the dosage range required depends on the precise nature of the antibody or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages are in the range of 5-20 mg per kg of body weight. The unit dosage can vary from less than 100 mg, but typically will be in the region of 250-2000 mg per dose, which may be administered daily or less frequently (e.g. on alternative days for up to 1 week)

It is also within the scope of the invention to use the antibodies of the invention in therapeutic methods for the prevention or treatment of CDI in combination with one another, or as an adjunct to, or in conjunction with, other established therapies normally used in the treatment in CDI. For example, the antibodies of the present invention may be administered in conjunction with a suitable antibiotic (e.g. metronidazole and/or vancomycin)

The combination treatment may be carried out in any way as deemed necessary or convenient by the person skilled in the art and for the purpose of this specification, no limitations with regard to the order, amount, repetition or relative amount of the compounds to be used in combination is contemplated.

Definitions Section

*Clostridium difficile* is a species of Gram-positive bacteria of the genus Clostridium.

*Clostridium difficile* infection (CDI) means a bacterial infection which affects humans and animals and which results in a range of symptoms from mild self-limiting diarrhoea to life-threatening conditions such as pseudomembranous colitis and cytotoxic megacolon. In this disease, *C. difficile* replaces the normal gut flora and produces cytotoxins which attack and damage the gut epithelium. Primary risk factors for human CDI include: receiving broad-spectrum antibiotics, over 65 years old and hospitalised.

*Clostridium difficile* Toxin A is a family of protein cytotoxins/enterotoxins of approximately 300 kDa in size. Toxin A has an enzyme activity within the N-terminal which acts to disrupt the cytoskeleton of the mammalian cell causing cell death. There are a number of naturally occurring variants of Toxin A within the strains of *Clostridium difficile* which are call 'toxinotypes'. The various toxinotypes of Toxin A have variations within their primary sequence of usually <10% overall. Examples of suitable Toxin A sequences include SEQ ID Nos: 1 and 3.

*Clostridium difficile* Toxin B is a family of protein cytotoxins of approximately 270 kDa in size which are similar to Toxin A but significantly more cytotoxic.

Like Toxin A, Toxin B has an enzyme activity within the N-terminal region which acts to disrupt the cytoskeleton of the mammalian cell causing cell death. There are a number of naturally occurring variants of Toxin B within the strains of *C. difficile* which are call 'toxinotypes'. The various toxinotypes of Toxin B have variations within their primary sequence of usually <15% overall. Examples of suitable Toxin A sequences include SEQ ID Nos: 2 and 4.

Binary Toxin is a two component cytotoxin produced by some but not all strains of *C. difficile*. The binary toxins are similar in action to *Clostridium botulinum* C2 and *Clostridium perfringens* iota toxins, which like *C. difficile* binary toxin, consist of a cell binding fragment of approximately 100 kDa and an enzymically active 'effector' fragment of approx. 50 kDa. Examples of suitable Binary Toxin sequences include SEQ ID Nos: 5 and 6.

As used herein, the term "toxin" encompasses said toxin fragments. The fragment may range from any number of amino acids between 10 and 2700 (e.g. at least 50, 100, 150, 200, 250, 300, 350, 400, 500, 750, 1000, 1500, 2000 or 2500) of the reference toxin. The fragment preferably includes at least one epitope of the gene product in question. The "fragment" may also have a common antigenic cross-reactivity and/or substantially the same in vivo biological activity as the toxin from which it is derived. For example, an antibody capable of binding to a fragment would be also capable of binding to the toxin from which it is derived. Alternatively, the fragment may share a common ability to induce a "recall response" of a T-lymphocyte which has been previously exposed to an antigenic component of a *C. difficile* toxin.

Reference to the term Toxin embraces "variants" thereof—for example, a peptide or peptide fragment having at least 80 or 85 or 90 or 95 or 96 or 97 or 98 or 99 percent amino acid sequence homology with a *C. difficile* Toxin. In a further embodiment, a "variant" may be a mimic of the peptide or peptide fragment, which mimic reproduces at least one epitope of the peptide or peptide fragment.

Reference to the Toxin embraces Toxin "toxoid", which is discussed in more detail below.

Toxinotypes are often used to classify strains of *C. difficile*. Toxinotypes are based on a method which characterises the restriction patterns obtained with the toxin genes. As described above, toxinotypes of Toxins A and B represent variants, by primary amino acid sequence, of these protein toxins.

*Clostridium difficile* Toxoid is used to describe a *C. difficile* toxin (Toxin A, Toxin B or Binary Toxin) or a mixture of *C. difficile* toxins that has been partially or completely inactivated. A toxin is considered inactivated if it has less toxicity (e.g. 100%, 99%, 95% or 90% less toxicity) than untreated toxin as measured by an in vitro cytotoxicity assay or by animal toxicity.

An antibody that binds to a toxin of interest is one capable of binding that toxin with sufficient affinity such that the antibody is useful as a therapeutic agent. An antibody that binds to a toxin of interest is one that binds to a toxin of *C. difficile* with an affinity ($K_a$) of at least $10^4$ M.

Toxin neutralising means the action of a substance (e.g. an antibody) which blocks the biological action of one or more of the cytotoxins (Toxin A and/or Toxin B and/or binary toxin) of *C. difficile*. The cytotoxin's biological action being defined as its ability to kill or impair the function of mammalian cells, in particular cells of the mammalian gut epithelium. Toxin neutralising activity of a substance may be measured by its ability to prevent the death of mammalian cells grown in culture.

A therapeutically effective amount refers to the amount of the antibody, which when administered alone or in combination to a patient for treating CDI, or at least one of the clinical symptoms of CDI, is sufficient to affect such treatment of the disease, or symptom. The therapeutically effective amount can vary depending, for example, on the antibody, the infection, and/or symptoms of the infection, severity of the infection, and/or symptoms of the infection, the age, weight, and/or health of the patient to be treated, and the judgment of the prescribing physician. An appropriate therapeutically effective amount in any given instance may be ascertained by those skilled in the art or capable of determination by routine experimentation. A therapeutically effective amount is also one in which any toxic or detrimental effects of the antibody are outweighed by the beneficial effects.

A "prophylactically effective amount" is any amount of the antibody that, when administered alone or in combination to a patient, inhibits or delays the onset or reoccurence of the CDI, or at least one of the clinical symptoms of CDI. In some embodiments, the prophylactically effective amount prevents the onset or reoccurence of the *Clostridium difficile* infection entirely. "Inhibiting" the onset means either lessening the likelihood of the infection's onset, or preventing the onset entirely.

Sheep means any species that falls within the *Ovis* genus (e.g. *Ovis ammon, Ovis orientalis aries, Ovis orientalis orientalis, Ovis orientalis vignei, Ovis Canadensis, Ovis dalli, Ovis nivicola*).

Goat means any species that falls within the *Capra* genus (e.g. e.g. *Capra pyrenaicais, Capra ibex, Capra nubiana, Capra sibirica, Capra walie, Capra caucasica, Capra cylindricornis Capra aegagrus, Capra falconed*).

An ovine antibody is an antibody that has at least 100%, 99%, 95%, 90%, 80%, 75%, 60%, 50%, 25% or 10% amino acid sequence identity to an antibody that has been raised in a sheep.

For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat'l. Acad. Sci. USA 85: 2444 (1988)], by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Wis. 53705), or by visual inspection [see Current Protocols in Molecular Biology, F. M. Ausbel et al, eds, Current Protocols, a joint venture between Greene Publishing Associates, In. And John Wiley & Sons, Inc. (1995 Supplement) Ausbubel].

Examples of algorithms suitable for determining percent sequence similarity are the BLAST and BLAST 2.0 algorithms [see Altschul (1990) J. Mol. Biol. 215: pp. 403-410; and "http://www.ncbi.nlm.nih.gov/" of the National Center for Biotechnology Information].

In a preferred homology comparison, the identity exists over a region of the sequences that is at least 10 amino acid, preferably at least 20 amino acid, more preferably at least 30 amino acid residues in length.

An "antibody" is used in the broadest sense and specifically covers polyclonal antibodies and antibody fragments so long as they exhibit the desired biological activity. In particular, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987, which are incorporated herein by reference).

Preferably, each VHC and VLC is composed of three CDRs and four FRs, arranged from amino-terminus to carboxy-terminus in the following order: FRI, CDRI, FR2, CDR2, FR3, CDR3, FR4.

The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region includes three domains, CHI, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

The term antibody, as used herein, also refers to a portion of an antibody that binds to a toxin of *C. difficile* (e.g. Toxin B), e.g., a molecule in which one or more immunoglobulin chains is not full length, but which binds to a toxin. Examples of binding portions encompassed within the term antibody include (i) a Fab fragment, a monovalent fragment consisting of the VLC, VHC, CL and CHI domains; (ii) a F(ab')$_2$ fragment, a bivalent fragment comprising two Fab fragments linked by a disulfide bridge at the hinge region; (iii) a Fc fragment consisting of the VHC and CHI domains; (iv) a Fv fragment consisting of the VLC and VHC domains of a single arm of an antibody, (v) a dAb fragment (Ward et al, Nature 341:544-546, 1989), which consists of a VHC domain; and (vi) an isolated complementarity determining region (CDR) having sufficient framework to bind, e.g. an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science IAI-ATi-Alβ; and Huston et al. (1988) Proc. Natl. Acad. ScL USA 85:5879-5883). Such single chain antibodies are also encompassed within the term antibody. These are obtained using conventional techniques known to those with skill in the art, and the portions are screened for utility in the same manner as are intact antibodies.

There now follows a brief description of the Figures, which illustrate aspects and/or embodiments of the present invention.

FIG. 1 Measurement of antibodies to Toxin A in serum by affinity chromatography. Antibody binding to Toxin A immobilised onto Sepharose gel which was subsequently eluted. The Figure shows the linear relationship between serum load and eluted Toxin A-specific antibody. Experimental details are provided in Example 9.

Figure 2:
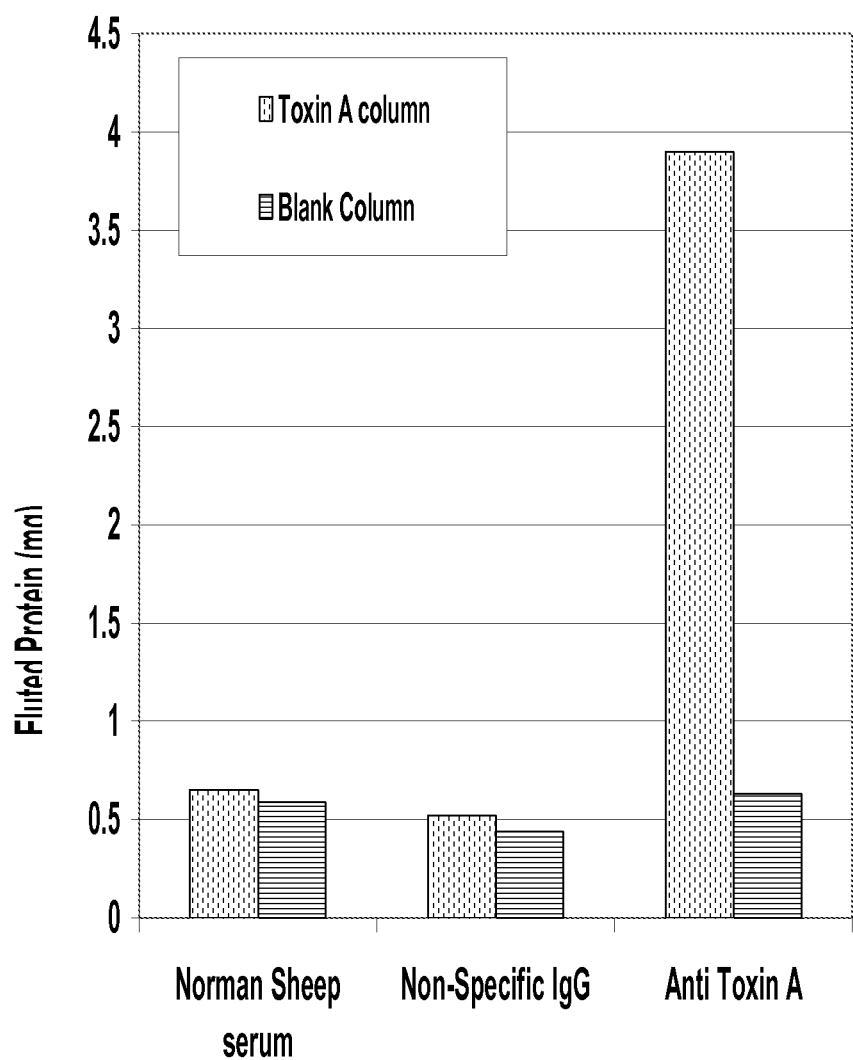

FIG. 2 Measurement of antibodies to Toxin A in serum by affinity chromatography. Antibody binding to Toxin A immobilised onto Sepharose gel which was subsequently eluted. The Figure demonstrates specific antibody in sheep immunised with a toxoid of Toxin A. Antibodies to Toxin A were present in the sheep serum at >3 mg/ml (3 g/liter). Experimental details are provided in Example 9.

Figure 3:
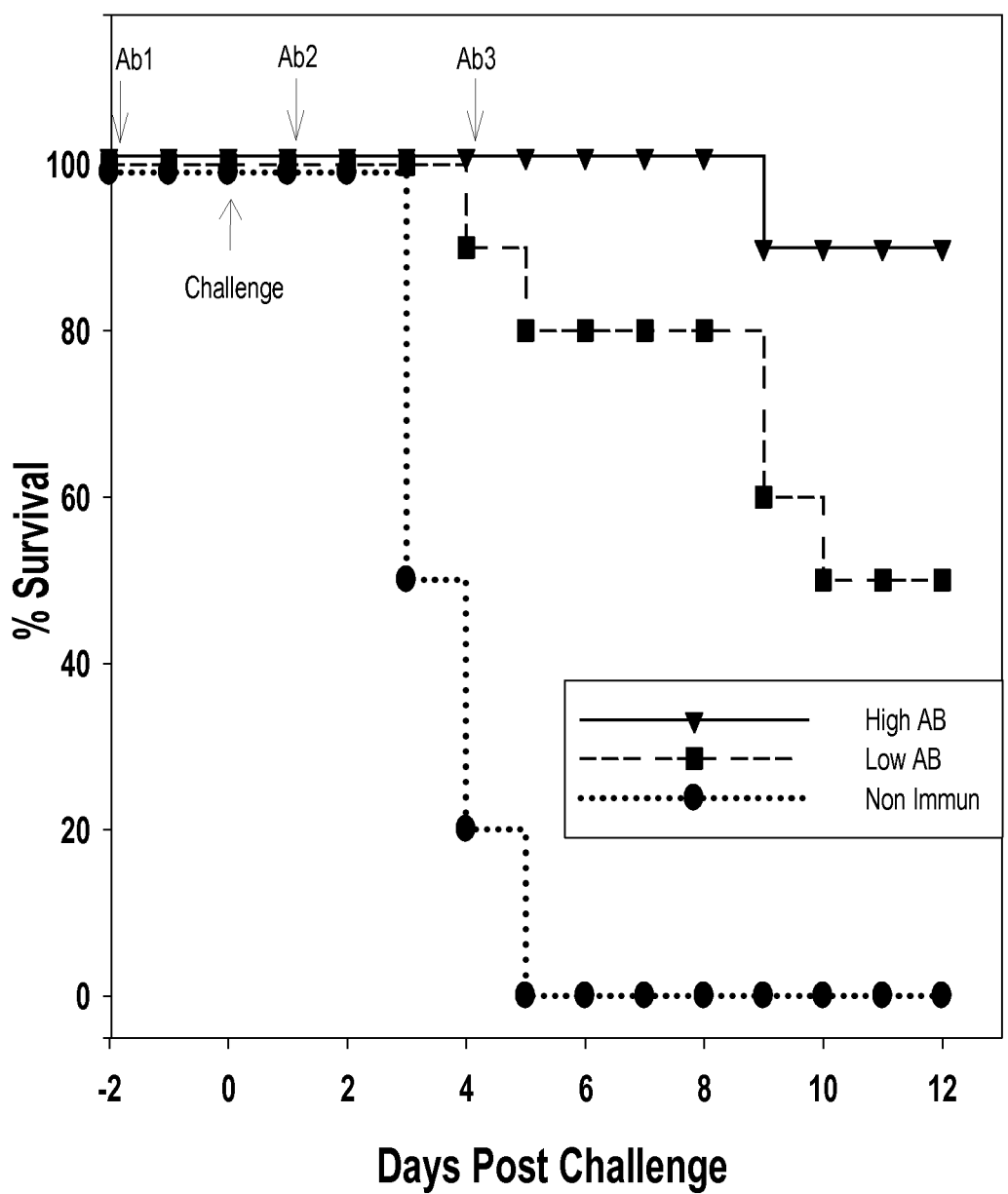

FIG. 3 Protection from CDI by passive immunisation with ovine anti *Clostridium difficile* Toxins A and B mixture. Syrian hamsters (groups of 10) were passively immunised (i.p.) with either ovine antibodies to Toxin A and B at 10 mg/dose (▼), 2 mg/dose (■) or with a non-specific control antibody (●) at the times indicated. Animals received clindamycin at Day −2 and at Day 0 were challenged with *C. difficile* spores ($2\times10^2$ colony forming units). Survival, days post challenge are shown by the plots.

Figure 4:
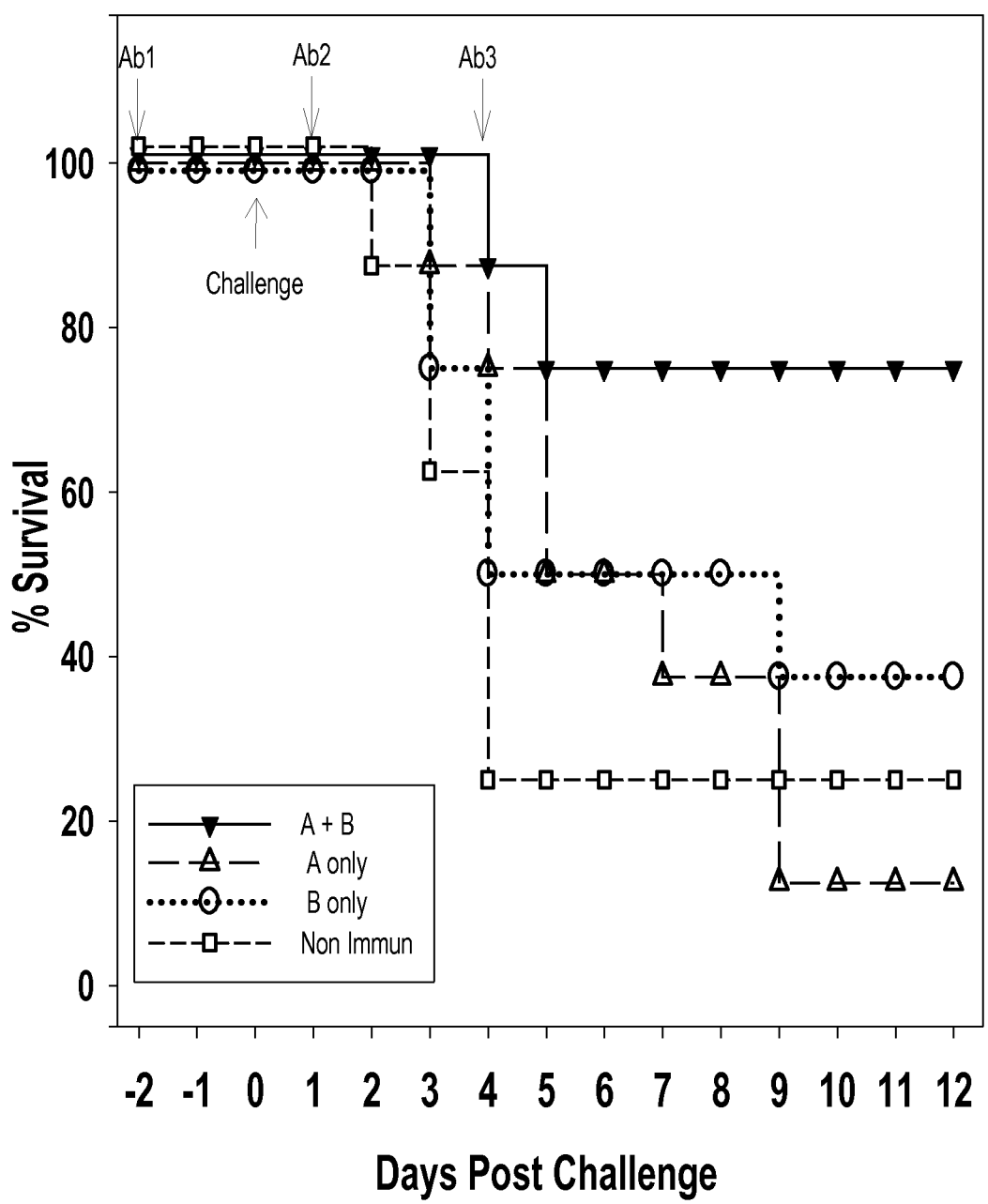

FIG. 4 Protection from CDI by passive immunisation with ovine anti *Clostridium difficile* Toxins A or B. Syrian hamsters (groups of 10) were passively immunised (i.p.) with either ovine antibodies to Toxin A+B at 10 mg/dose (▼), Toxin A antibodies alone at 10 mg/dose (Δ), Toxin B antibodies alone at 10 mg/dose (○) or with a non-specific control antibody (□) at the times indicated. Animals received clindamycin at Day −2 and at Day 0 were challenged with *C. difficile* spores ($2\times10^2$ colony forming units). Survival, days post challenge are shown by the plots.

Figure 5:
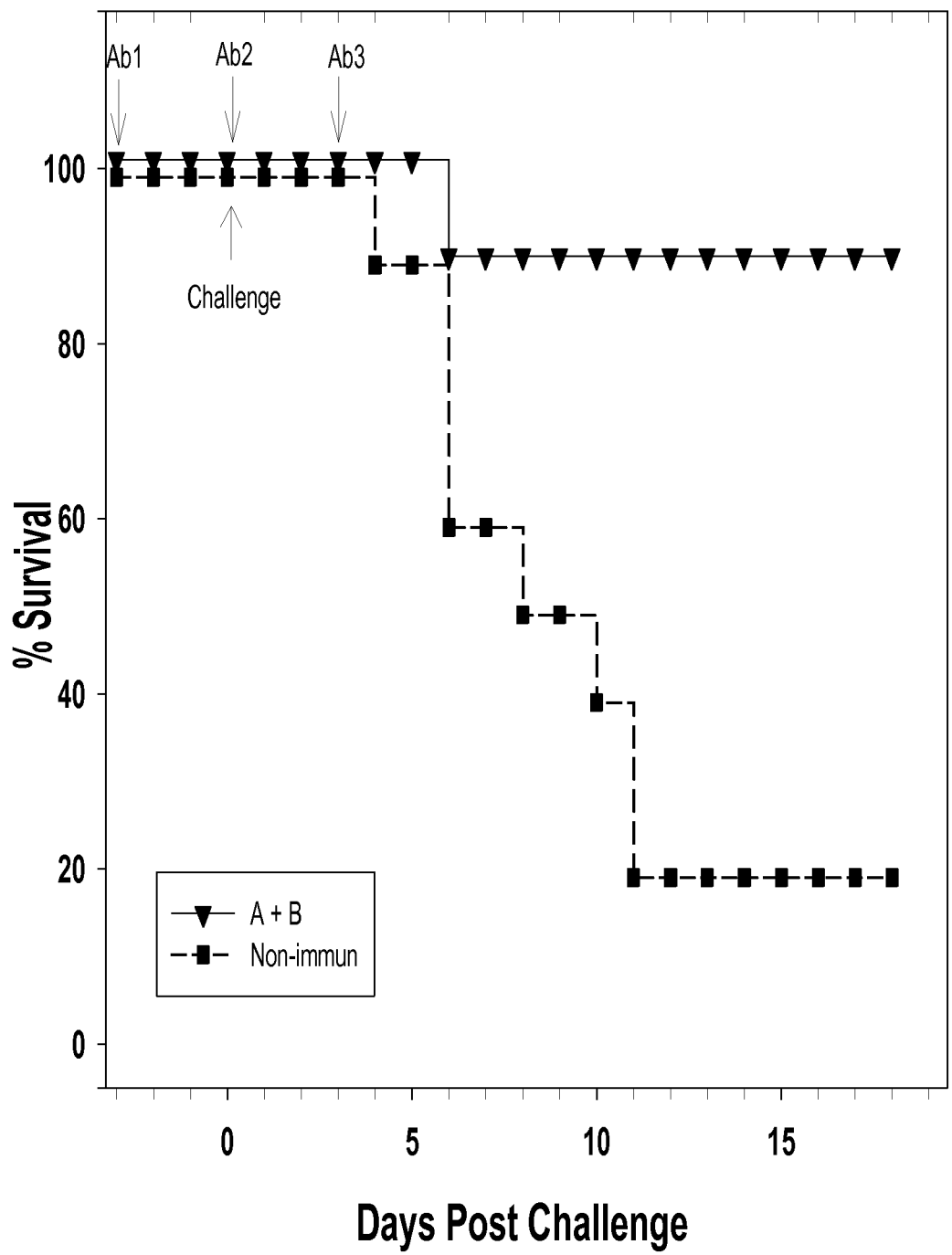

FIG. 5 Protection from CDI induced by the 027 Ribotype, 'hypervirulent' *Clostridium difficile* (strain R20291, Stoke Mandeville) by passive immunisation with ovine anti *Clostridium difficile* Toxins A and B mixture. Syrian hamsters (groups of 10) were passively immunised (i.p.) with either ovine antibodies to Toxin A and B at 10 mg/dose (▼) or with a non-specific control antibody (■) at the times indicated. Animals received clindamycin at Day −3 and at Day 0 were challenged with *C. difficile* spores ($1\times10^3$ colony forming units). Disease states at days post challenge are shown by the plots.

Figure 6:
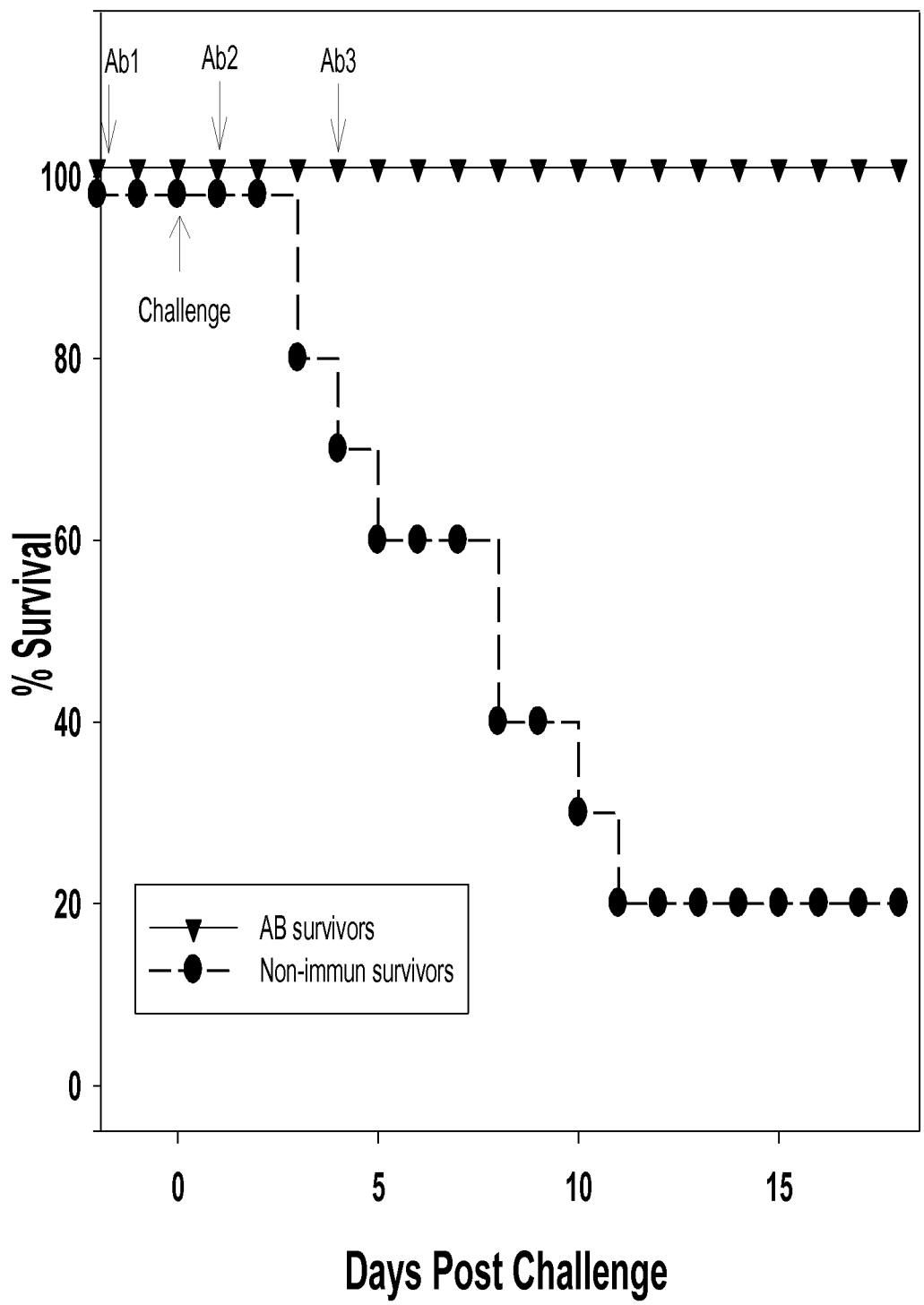

FIG. 6 Protection from CDI induced by the 078 Ribotype, 'hypervirulent' *Clostridium difficile* (Toxinotype 5) by passive immunisation with ovine anti *Clostridium difficile* Toxins A and B mixture. Syrian hamsters (groups of 10) were passively immunised (i.p.) with either ovine antibodies to Toxin A and B at 10 mg/dose (▼) or with a non-specific control antibody (●) at the times indicated. Animals received clindamycin at Day −2 and at Day 0 were challenged with *C. difficile* spores ($2\times10^3$ colony forming units). Disease states at days post challenge are shown by the plots.

SUMMARY OF EXAMPLES

Example 1 Purification of *C. difficile* Toxins A and B of Toxinotype 0

Example 2 Purification of *C. difficile* Toxins A and B of other Toxinotypes

Example 3 Purification of recombinant *C. difficile* Toxins A and B

Example 4 Purification of *C. difficile* binary toxin

Example 5 Preparation of Toxoids of *C. difficile* Toxins A and B

Example 6 Preparation of antiserum

Example 7 Preparation of antiserum to Toxins A and B of toxinotype 0

Example 8 Assessment of the neutralising efficacy for antisera to toxins using the in vitro cell assay Example 9 Quantifying the amount of specific antibody to *C. difficile* toxins in serum using immunoaffinity columns Example 10 Preparation of antibody mixtures Example 11 Assessment of the in vivo efficacy of ovine antibodies for preventing CDI Example 12 Assessment of the in vivo efficacy of ovine antiserum for treating CDI Example 13 Clinical uses of antibody formulations Example 14 Protection from CDI by passive immunisation with ovine anti-*Clostridium difficile* Toxins A and B antibody mixture Example 15 Protection from CDI by passive immunisation with ovine anti-*Clostridium difficile* Toxins A or B antibodies, or with ovine anti-*Clostridium difficile* Toxins A and B antibody mixture Example 16 Protection from CDI induced by the 027 Ribotype, 'hypervirulent' *Clostridium difficile* (strain R20291, Stoke Mandeville) by passive immunisation with ovine anti-*Clostridium difficile* Toxins A and B mixture Example 17 Protection from CDI induced by the 078 Ribotype, 'hypervirulent' *Clostridium difficile* isolate by passive immunisation with ovine anti-*Clostridium difficile* Toxins A and B mixture

SUMMARY OF SEQ ID NOS

Where an initial Met amino acid residue or a corresponding initial codon is indicated in any of the following SEQ ID NOs, said residue/codon is optional.

1. Protein sequence of *Clostridium difficile* Toxin A- Toxinotype 0
2. Protein sequence of *Clostridium difficile* Toxin B- Toxinotype 0
3. Protein sequence of *Clostridium difficile* Toxin A- Toxinotype III
4. Protein sequence of *Clostridium difficile* Toxin B- Toxinotype III
5. Protein sequence of *Clostridium difficile* Binary toxin fragment A
6. Protein sequence of *Clostridium difficile* Binary toxin fragment B

EXAMPLES

Example 1

Purification of *Clostridium difficile* Toxins A and B of Toxinotype 0

A *C. difficile* strain producing Toxinotype 0 Toxins A and B (e.g. VPI 10463) was grown in dialysis sac culture as described (Roberts and Shone (2001) Toxicon 39: 325-333). After growth, the cell slurry was collected from the dialysis sacs and then centrifuged for 10000×g for 30 min and the pH of the resulting supernatant fluid adjusted to pH 7.5 and made 70% saturated with respect to ammonium sulphate. The precipitate containing the toxins was collected by centrifugation then resuspended in 50 mM bistris pH 6.5 buffer and dialysed against the same buffer at 4° C. After dialysis, the solution of crude Toxins A and B was purified by chromatography on Q Sepharose, anion exchange chromatography and the protein peaks containing the toxins eluted with a gradient of NaCl. The peak containing Toxin A was dialysed against 50 mM Hepes pH 7.4 buffer containing 0.5 M NaCl and purified on a Zn chelating column (Zn Sepharose). After loading the toxin and washing the contaminating proteins from the column, the purified Toxin A was eluted with a buffer containing 50 mM Hepes pH 7.4, 20 mM EDTA and 0.1M NaCl. The purified Toxin A was dialysed against 50 mM Hepes pH 7.4 buffer containing 0.15 M NaCl and stored at 4° C. or frozen until use. The peak containing the Toxin B from the initial Q Sepharose column was further purified by chromatography on a column of high resolution Mono Q anion exchange resin. After loading the toxin onto the column in 50 mM bistris pH 6.5 buffer, the purified Toxin B was eluted with a NaCl gradient and the fractions containing the toxin pooled. The purified Toxin B was dialysed against 50 mM Hepes pH 7.4 buffer containing 0.15 M NaCl and stored at 4° C. or frozen until use.

Example 2

Purification of *C. difficile* Toxins A and B of other Toxinotypes

Toxins A and B representing any of the known Toxinotypes may be purified as described in Example 1. Known *C. difficile* strains producing Toxins A and B of various toxinotypes are given in Table 1 and by selecting the required strain for purification, Toxins A and B of the required Toxinotype may be purified. Alternatively, *C. difficile* may be toxinotyped as described previously (Rupnik et al. (1998) J. Clinical Microbiol. 36: 2240-2247; Rupnik et al. (2001) Microbiology 147: 439-447) until a *C. difficile* strain producing toxin of the desired toxinotype is obtained To produce Toxinotype III Toxins A and B, *C. difficile* strain R20291 (also known as NCTC 13366) was grown in dialysis sac culture as described (Roberts and Shone (2001) Toxicon 39: 325-333) and the toxins purified as described in Example 1.

Example 3

Purification of recombinant *C. difficile* Toxins A and B

Amino acid sequences of examples of the *C. difficile* Toxins A and B are shown Seq IDs 1 to 4. Genes encoding these peptides may made commercially with codon bias for any desired expression host (e.g. *E. coli, Pichia pastoris*). Peptides are expressed from these genes using standard molecular biology methods (e.g. Sambrook et al. 1989, Molecular Cloning a Laboratory Manual, Second Edition, Cold Spring Harbor Laboratory Press, Cold Spring Harbor, N.Y.) and the resulting soluble expressed polypeptides are purified by a combination of hydrophobic interaction chromatography, ion exchange chromatography and ceramic hydroxyl apatite chromatography. Other chromatographic techniques well known to the art of protein purification, such as size exclusion chromatography and/or affinity chromatography, may be used. For the latter, recombinant fragments may be expressed with affinity purification tags (e.g. Histidine-6, streptag) such as described in the pET vector Expression System Manual, 11th Edition published by Merck KGaA, Darmstadt, Germany.

To produce a recombinant toxin from a *C. difficile* toxinotype for which the sequence is unknown, it will be necessary to first extract the DNA and derive the toxin sequence(s) by standard molecular biology methods. Once the sequence has been derived, the recombinant toxin may be expressed from a synthetic gene as above.

Example 4

Purification of *C. difficile* binary toxin

Amino acid sequences of the *C. difficile* binary toxin fragments A and B are shown Seq IDs 5 and 6, respectively. Genes encoding these peptides may made by commercially with codon bias for any desired expression host (e.g. *E. coli, Pichia pastoris*). Peptides are expressed from these genes using standard molecular biology methods (e.g. Sambrook et al. 1989, Molecular Cloning a Laboratory Manual, Second Edition, Cold Spring Harbor Laboratory Press, Cold Spring Harbor, N.Y.) and the resulting soluble expressed peptides are purified by a combination of hydrophobic interaction chromatography, ion exchange chromatography and ceramic hydroxyl apatite chromatography. Other chromatographic techniques well known to the art of protein purification, such as size exclusion chromatography and/or affinity chromatography, may be used. Alternatively, recombinant fragments may also be expressed with affinity purification tags (e.g Histidine-6, streptag) such as described in the pET vector Expression System Manual, 11th Edition published by Merck KGaA, Darmstadt, Germany.

If the peptides are produced in an insoluble form then they may be expressed with a histidine-6 purification tag using a commercially available expression vector such as pET52b and refolded by on-column refolding techniques as described by the review of Lia et al. and references contained therein (Lia M et al (2004) Protein Expression & Purification 33, 1-10), which is hereby incorporated by reference thereto.

Example 5

Preparation of Toxoids of *C. difficile* Toxins A and B

Purified *C. difficile* toxins at a concentration of between 0.2-2 mg/ml are dialysed against a suitable buffer (e.g. 10 mM Hepes buffer pH 7.4 containing 150 mM NaCl) and then formaldehyde added at a final concentration of between 0.05 and 0.5% and incubated for between 1 and 25 days at 35° C. After incubation, the formaldehyde is removed by dialysis. Conditions for the treatment with formaldehyde may vary between peptides and final conditions may be fine-tuned on the basis of outcome of protective efficacy evaluations.

Example 6

Preparation of Antiserum

A number of factors are taken into consideration during the preparation of antiserum in order to achieve the optimal humoral antibody response. These include:
breed of animal
choice of adjuvant
number and location of immunisation sites
quantity of immunogen
number of and interval between doses As a result of optimising these parameters it is routine to obtain specific antibody levels in excess of 6 g/liter of serum.

For sheep, 2 ml of buffer solution containing between 10 and 500 µg of *C. difficile* antigen is mixed with 2.6 ml of Freund's adjuvant. The complete form of the adjuvant is used for the primary immunisation and incomplete Freund's adjuvant for all subsequent boosts. Mixing of the adjuvant is carried out for several minutes to ensure a stable emulsion. About 4.2 ml of the antigen/adjuvant mixture is used to immunise each sheep by inn injection and spread across 6 sites including the neck and all the upper limbs. This is repeated every 28 days. Blood samples are taken 14 days after each immunisation. Once adequate antibody levels are achieved, larger volumes are taken (10 ml/kg body weight) into sterile bags. The bags are rotated slowly to accelerate clotting, centrifuged for 30 min at 4500×g and the serum removed under aseptic conditions and pooled. Any animal showing low titres to the desired *C. difficile* antigen is removed from the flock.

Example 7

Preparation of Antiserum to Toxins A and B of Toxinotype 0

Toxins A and B from a toxinotype 0 strain (e.g. VPI 10463) were prepared as described in Example 1. Alternatively, Toxin A or B may be made by recombinant methods as described by Yang et al. (Yang G, Zhou B, Wang J, He X, Sun X, Nie W, Tzipori S, Feng H (2008) Expression of recombinant *Clostridium difficile* toxin A and B in Bacillus megaterium. BMC Microbiol. 8: 192). Purified Toxins may be toxoided as described in Example 5.

For immunisation of sheep with Toxoids A or B, 2 ml of buffer solution containing between 10 and 500 µg of either *C. difficile* Toxoids A or B was mixed with 2.6 ml of Freund's adjuvant. The complete form of the adjuvant was used for the primary immunisation and incomplete Freund's adjuvant used for all subsequent boosts. Mixing of the adjuvant was carried out for several minutes to ensure a stable emulsion. After mixing, approx 4.2 ml of the antigen/adjuvant mixture was used to immunise each sheep by im injection and spread across 6 sites including the neck and all the upper limbs. This was repeated every 28 days and serum samples collected 14 days after each immunisation. Once adequate antibody levels were achieved, larger production sample were taken (10 ml /kg body weight) into sterile bags. The bags were rotated slowly to accelerate clotting, centrifuged for 30 min at 4500×g and the serum removed under aseptic conditions and pooled. Any animal showing low titres to either Toxins A or B was omitted from the flock.

Example 8

Assessment of the Neutralising Efficacy for Antisera to Toxins Using the in vitro Cell Assay The toxin neutralizing activity of the antisera against *C. difficile* Toxins is measured by cytotoxicity assays using Vero cells. A fixed amount of either purified *C. difficile* Toxin A or Toxin B is mixed with various dilutions of the antibodies, incubated for 1 h at 37° C. and then applied to Vero cells growing on 24-well tissue culture plates. Both Toxin A and B possess cytotoxic activity which results in a characteristic rounding of the Vero cells over a period of 24-72 h. In the presence of neutralising antibodies this activity is inhibited and the neutralising strength of an antibody preparation may be assessed by the dilution required to neutralise the effect of a designated quantity of either Toxin A or B.

Data demonstrating the neutralising activity of ovine antibody to *C. difficile* Toxin A is shown in Table 2. In this experiment, various dilutions of ovine antibody were mixed with Toxin A at a final concentration of 50 ng/ml and incubated for 1 h at 37° C. and then applied to Vero cells as above and incubated at 37° and monitored over a period of 24 -72 h. The antibody dilutions which protect the cells against the cytotoxic effects of the Toxin A were calculated. Table 2 shows that sheep immunised for a period of 14 weeks had a neutralising titre of 16000 (i.e. a ¹⁄₁₆₀₀₀ dilution of the serum protected the cells from the cytotoxic effects of Toxin A).

TABLE 2

Neutralisation Titres of Ovine Antibodies Raised Against Formaldehyde-Treated Toxin A:

| Number of vaccinations | Immunisation period (weeks) | Antibody Neutralising Titre¶ |
|---|---|---|
| 0 | 0 | <10 |
| 1 | 0 | <10 |
| 2 | 6 | 2000 |
| 3 | 10 | 4000 |
| 4 | 14 | 16000 |

¶Dilution of serum required to neutralise 50 ng/ml of Toxin A in cell neutralisation assays

TABLE 3

Neutralisation Titres of Ovine Antibodies Raised Against Formaldehyde-Treated Toxin B:

These data (below) show that higher immunising doses of Toxoid B antigen results in a better ovine toxin-neutralising immune response as measured by Vero cell cytotoxicity assays. The assays employed are described immediately above in Example 8.

| Immunising dose (μg) of C. difficile Toxoid B | Neutralisation titre against Toxin B in cell assays¶ |
|---|---|
| Sheep anti toxoid B (10 ug) | 1/1280 |
| Sheep anti toxoid B (50 ug) | 1/2560 |
| Sheep anti toxoid B (250 ug) | 1/10240 |

All animals were given 2 doses of formaldehyde-treated Toxin B

¶Dilution of serum required to completely neutralise 0.5 ng/ml of Toxin B in cell neutralisation assays

TABLE 4

Neutralisation Titres of Ovine Anti Toxin B against equivalent concentrations of Toxin B from Toxinotype 0 and Toxinotype III
These data (below) compare the capacity of ovine antibody raised against Toxoid B derived from Toxin B (Toxinotype 0) to neutralise equivalent amounts of Toxin B (Toxinotype 0) and Toxin B (Toxinotype III). Toxin B (Toxinotype 0) and Toxin B (Toxinotype III) were purified from *C. difficile* strains VPI 10463 and R20291, respectively.
Cell assays were performed as described immediately above in Example 8 using equivalent cytotoxic amounts of each Toxin B type. Titrations were carried out on Toxin B fixed at 4 units (4 fold the amount required to induce cell death) in one experiment and 10 units in another experiment. The data show that the ovine antibody raised against Toxin B, using a Toxoid B derived from Toxinotype 0 strain, neutralised Toxin B (Toxinotype 0) and Toxin B (Toxinotype III) with the same efficacy.

| | Ovine anti Toxin B - Neutralisation Titre | |
|---|---|---|
| Toxinotype | 4 units Toxin B | 10 units toxin B |
| Toxin B - Toxinotype 0 | 2560 | 1280 |
| Toxin B - Toxinotype III | 2560 | 1280 |
| Relative titre (0:III) | 1 | 1 |

TABLE 5

Neutralisation Titres of Ovine Anti Toxin B against equivalent concentrations of Toxin B from Toxinotype 0 and Toxinotype V
These data compare the capacity of ovine antibody raised against Toxoid B derived from Toxin B (Toxinotype 0) to neutralise equivalent amounts of Toxin B (Toxinotype 0) and Toxin B (Toxinotype V). Toxin B (Toxinotype 0) and Toxin B (Toxinotype V) were purified from *C. difficile* strains VPI 10463 and a *C. difficile* ribotype 078 isolate, respectively.
Cell assays were performed as in Example 8 using equivalent cytotoxic amounts of each Toxin B type. Titrations were carried out on Toxin B fixed at 4 units (4 fold the amount required to induce cell death) in one experiment and 10 units in another experiment.
The data show that the ovine antibody raised against Toxin B, using a Toxoid B derived from Toxinotype 0 strain, neutralised Toxin B (Toxinotype 0) and also Toxin B (Toxinotype V) with 2-fold reduced efficiency.

| | Ovine anti Toxin B - Neutralisation Titre | |
|---|---|---|
| Toxinotype | 4 units Toxin B | 10 units toxin B |
| Toxin B - Toxinotype 0 | 2560 | 1280 |
| Toxin B - Toxinotype V | 1280 | 640 |
| Relative titre (0:V) | 2 | 2 |

Example 9

Quantifying the Amount of Specific Antibody to *C. difficile* Toxins in Serum Using Immunoaffinity Columns Column Preparation The required amount of CNBr-activated Sepharose 4 Fast Flow (0.5 g dry weight) is weighed into a suitable clean container (glass or plastic). About 10 ml of diluted hydrochloric acid (1 mM) is added to swell the gel and, after 20-30 min, the gel is transferred to a 10-mL glass column and washed with a further 20 mL of HCl (1 mM), followed by 20 mL of coupling buffer (sodium bicarbonate, 100 mM, pH 8.3, containing 500 mM sodium chloride). Toxin (Toxin A, Toxin B or a binary toxin fragment solution (1 mL) at a concentration of 1 mg/mL is diluted to 5 mL with coupling buffer and added to the column containing the activated gel and the contents mixed gently until the gel is re-suspended and rotated at room temperature overnight (16-18 hr). The column is then drained and 5 ml of blocking reagent (ethanolamine solution, 1M) added, mixed gently and rotated for 2hr at room temperature. Next, the column is washed with 20 mL coupling buffer followed by 20 mL of elution buffer (glycine solution 100 mM, pH 2.5). This step is repeated twice. The column is finally washed with 20 mL of assay buffer (sodium phosphate buffer, 10 mM, pH 7.4 containing 500 mM sodium chloride and sodium azide at a final concentration of 1g/L) and stored in 3-5 mL of assay buffer at 2-8° C. until used.

Column Assessment

The specific binding and non-specific capacity of the column must be assessed prior to use. The column is removed from the refrigerator and allowed to equilibrate to room temperature and then washed with 25 mL of assay buffer. Increasing volumes of the product (whole antisera, purified IgG, Fab or F(ab')$_2$) are individually loaded onto the column and mixed end-over-end gently for 1 hr at room temperate. The unbound fraction is washed off with 25 mL of assay buffer and the bound fraction then eluted from the column with 20 ml of elution buffer (glycine buffer 100 mM, pH 2.5). The protein content of the eluted fraction is determined spectrophotometrically at 280 nm using an extinction coefficient relevant to the product namely 1.5 for sheep IgG (Curd et al., 1971) or 1.4 for sheep Fab and F(ab')$_2$ (Allen, 1996). A saturation curve is obtained by plotting the amount of eluted protein against the volume loaded.

Non-specific binding (NSB) is assessed using normal sheep serum (NSS) prior to immunisation. Thus it is necessary to differentiate between this and binding due to some specific antibodies in normal serum (since all animals will have been exposed to *C. difficile*). FIG. 1 demonstrates the typical binding capacity curve showing an increase in specific binding as a result of increasing the antiserum loading volume. There is a little change in non-specific binding (NSB) with the increase of loading volume. The 0.5 g (1.5-2.0 mL swelled gel) contain 1 mg of toxin (coupling ratio of 2 mg/g) is sufficient for the volume of specific antisera (0.5-4 mL) loaded. However 1 ml is the recommended loading volume for easy and convenient calculations.

The coefficient of variation for 10 replicates (between assay CV) is approximately 6%. There is no decline in the column capacity with time (estimated when used 80-100 times). This indicates that there is no leaching of the toxin from the column.

Affinity Column for Product Assessment

The column is used for GMP/GLP assessment of in-process and final product viz whole antisera, purified IgG, Fab and $F(ab')_2$. It is also used to assess and monitor the immune response of the immunised animals and to detect antitoxin antibodies in human samples.

The column is removed from the refrigerator and allowed to equilibrate to room temperature when it is washed with 25 mL of assay buffer. Product (1 mL) is added to the column and mixed end-over-end gently for 1hr at room temperature following which the unbound fraction is washed off with 25 mL of assay buffer (sodium phosphate buffer, 10 mM, pH 7.4 containing 500 mM sodium chloride and sodium azide at a final concentration of 1 g/L). The bound fraction is then eluted with 20 ml of elution buffer (glycine buffer 100 mM, pH 2.5) and its protein content determined spectrophotometrically at 280 nm using an extinction coefficient relevant to the product. FIG. 2 shows the analysis of serum from sheep immunised with a toxoid of Toxin A.

Example 10

Preparation of Antibody Mixtures

Antibodies will be blended to form the final product such that the required neutralising activities against Toxins A and B and their various isoforms (toxinotypes) are present in the final mixture.

Antibodies prepared against the various *C. difficile* toxinotypes may be blended in order to provide similar cross-protective efficacy as assessed in Example 10. For example, to provide similar cross-protection against *C. difficile* Toxin B derived from Toxinotypes 0 and III, antibodies may be mixed in a various proportions (e.g. 1:1, 2:1, 1:2 ratios) in order to provide similar specific neutralising activity against each of the Toxin B toxinotypes.

Example 11

Assessment of the in vivo Efficacy of Ovine Antibodies for Preventing CDI

To demonstrate the prophylactic (preventative) efficacy of antibodies against CDI in vivo, Syrian hamsters are passively immunised with ovine antibodies which have neutralising activity against one or more of the toxins of *C. difficile*. For assessing the prophylactic efficacy, hamsters will be given antibody either intravenously or by the intraperitoneal route at various times from 96 hours pre-challenge to 240 hours post challenge with *C. difficile*

Passively immunised hamsters are administered with a broad spectrum antibiotic (e.g. clindamycin) and 12-72 h later challenged with *C. difficile* spores by mouth. Animals are then monitored for up to 15 days for symptoms of *C. difficile*-associated disease. Control, non-immunised animals develop signs of the disease (e.g. diarrhoea, swollen abdomen, lethargy, ruffled fur) while those passively immunised with ovine antibody appear normal.

Example 12

Assessment of the in vivo efficacy of ovine antiserum for treating CDI

To demonstrate the efficacy of antiserum to treat CDI in vivo, Syrian hamsters are passively immunised with ovine antibodies which have neutralising activity against one or more of the toxins of *C. difficile*. For assessing the efficacy of a treatment formulation, hamsters will be given antibody either intravenously or by the intraperitoneal route at various times from 6 hours post-challenge to 240 hours post challenge with *C. difficile*

Prior to passively immunisation hamsters are administered with a broad spectrum antibiotic (e.g. clindamycin) and 12-72 h later challenged with *C. difficile* spores by mouth. Animals are then monitored for up to 15 days for symptoms of *C. difficile*-associated disease. Control, non-immunised animals develop signs of the disease (e.g. diarrhoea, swollen abdomen, lethargy, ruffled fur) while those treated with ovine antibody appear normal.

Example 13

Clinical Use of Antibody Formulations

Three examples serve to illustrate the therapeutic value of the systemic ovine products in patients with differing degrees of severity in their CDI.

Mild CDI

A 67 year old male is admitted to a coronary care unit following a severe myocardial infarction. He is making an uneventful recovery when he developes a mild diarrhoea without any other signs or symptoms. Because there are been recent episodes of CDI in the hospital, a faecal sample is sent immediately for testing and is found to contain both Toxin A and Toxin B. After isolation to a single room with its own toilet he receives 250 mg of the ovine $F(ab')_2$ intravenously followed by a second injection two days later. His diarrhoea stops quickly and he makes a full recovery without the need of either metranidazole or vancomycin.

Severe CDI with Risk of Relapse

A female aged 81 falls in her home and sustains a fractured left hip. She is immediately admitted to hospital and the hip is pinned successfully. Her frail condition prevents early discharge and, a few days later, she developes a productive cough for which she is given a wide spectrum antibiotic. After a further eight days she develops profuse diarrhoea with abdominal pain and tenderness and CDI is diagnosed by the appropriate faecal tests. At the time there is also evidence of systemic manifestations of the infection including a markedly raised white blood cell count, and of significant fluid loss with dehydration. The patient is started immediately on oral vancomycin and, at the same time, receives the first of five daily injections of 250 mg of the ovine F(ab')$_2$—based product intravenously. There is a rapid resolution of the signs and symptoms and of the laboratory manifestations of CDI. However, in order to avoid the risk of relapse of her CDI following stopping vancomycin, she continues to be treated for a further two weeks on an oral form of the antibody therapy. She experiences no relapse.

Severe CDI with Complications

An 87 year old female develops bronchopneumonia while resident in long-stay care facilities. The local general practitioner starts her on a course of antibiotic therapy with immediate benefit. However, eight days after stopping the antibiotic she experiences severe diarrhoea. Her condition starts to deteriorate necessitating admission to hospital where Toxin A is detected in her faeces by an ELISA test. By this time she is extremely ill with evidence of circulatory failure and her diarrhoea has stopped. The latter is found to be due to a combination of paralytic ileus and toxic megacolon and an emergency total colectomy is considered essential. Since such surgery is associated with a mortality in excess of 60% she receives intravenous replacement therapy together with the contents of two ampoules (500 mg) of product. By the time she is taken to the operating theatre four hours later, her general condition has improved significantly and she survives surgery.

Example 14

Protection from CDI by Passive Immunisation with Ovine Anti-*Clostridium difficile* Toxins A and B Antibody Mixture Syrian hamsters (groups of 10) were passively immunised (i.p.) with either ovine antibodies to Toxin A and B at 10 mg/dose (▼), 2 mg/dose (■) or with a non-specific control antibody (●) at the times indicated. Animals received clindamycin at Day −2 and at Day 0 were challenged with *C. difficile* spores ($2\times10^2$ colony forming units). Survival, days post challenge are shown by the plots.

The data (see FIG. 3) clearly show that passive immunisation with a mixture of ovine antibodies to Toxins A and B affords protection from CDI. In this experiment, 90% of animal given the high antibody dose were asymptomatic at 12 days post challenge.

Example 15

Protection from CDI by Passive Immunisation with Ovine Anti-*Clostridium difficile* Toxins A or B Antibodies, or with Ovine Anti-*Clostridium difficile* Toxins A and B Antibody Mixture Syrian hamsters (groups of 10) were passively immunised (i.p.) with either ovine antibodies to Toxin A+B at 10 mg/dose (▼), Toxin A antibodies alone at 10 mg/dose (Δ), Toxin B antibodies alone at 10 mg/dose (○) or with a non-specific control antibody (□) at the times indicated. Animals received clindamycin at Day −2 and at Day 0 were challenged with *C. difficile* spores ($2\times10^2$ colony forming units). Survival, days post challenge are shown by the plots.

The data (see FIG. 4) show that with respect to protection against CDI, the efficacy of a mixture of Toxin A+B antibodies is significantly better than either antibody given alone.

Example 16

Protection from CDI Induced by the 027 Ribotype, 'Hypervirulent' *Clostridium difficile* (strain R20291, Stoke Mandeville) by Passive Immunisation with Ovine Anti-*Clostridium difficile* Toxins A and B Mixture Syrian hamsters (groups of 10) were passively immunised (i.p.) with either ovine antibodies to Toxin A and B at 10 mg/dose (▼) or with a non-specific control antibody (■) at the times indicated. Animals received clindamycin at Day −3 and at Day 0 were challenged with *C. difficile* spores ($1\times10^3$ colony forming units). Disease states at days post challenge are shown by the plots.

The data (see FIG. 5) clearly show that passive immunisation with a mixture of ovine antibodies to Toxins A and B affords protection from CDI induced by the 027, 'hypervirulent *C. difficile* (strain R20291, stoke Mandeville). In this experiment, 90% of animal given Toxin NB antibody were asymptomatic at 18 days post challenge while 80% of the non-immunised controls showed severe symptoms of CDI.

Example 17

Protection from CDI Induced by the 078 Ribotype, 'Hypervirulent' *Clostridium difficile* Isolate by Passive Immunisation with Ovine Anti-*Clostridium difficile* Toxins A and B Mixture Syrian hamsters (groups of 10) were passively immunised (i.p.) with either ovine antibodies to Toxin A and B at 10 mg/dose (▼) or with a non-specific control antibody (●) at the times indicated. Animals received clindamycin at Day −2 and at Day 0 were challenged with *C. difficile* spores ($2\times10^3$ colony forming units). Disease states at days post challenge are shown by the plots.

The data (see FIG. 6) clearly show that passive immunisation with a mixture of ovine antibodies to Toxins A and B affords protection from CDI induced by the 078, 'hypervirulent *C. difficile*. In this experiment, 100% of animal given Toxin A/B antibody were asymptomatic at 18 days post challenge while 80% of the non-immunised controls showed severe symptoms of CDI.

SEQ ID NOs

1. *Clostridium difficile* Toxin A - Toxinotype 0

```
MSLISKEELIKLAYSIRPRENEYKTILTNLDEYNKLTTNNNENKYLQLKKLNESIDVFMNKYKTSSRNR
ALSNLKKDILKEVILIKNSNTSPVEKNLHFVWIGGEVSDIALEYIKQWADINAEYNIKLWYDSEAFLVN
TLKKAIVESSTTEALQLLEEEIQNPQFDNMKFYKKRMEFIYDRQKRFINYYKSQINKPTVPTIDDIIKS
HLVSEYNRDETVLESYRTNSLRKINSNHGIDIRANSLFTEQELLNIYSQELLNRGNLAAASDIVRLLAL
KNFGGVYLDVDMLPGIHSDLFKTISRPSSIGLDRWEMIKLEAIMKYKKYINNYTSENFDKLDQQLKDNF
KLIIESKSEKSEIFSKLENLNVSDLEIKIAFALGSVINQALISKQGSYLTNLVIEQVKNRYQFLNQHLN
PAIESDNNFTDTTKIFHDSLFNSATAENSMFLTKIAPYLQVGFMPEARSTISLSGPGAYASAYYDFINL
QENTIEKTLKASDLIEFKFPENNLSQLTEQEINSLWSFDQASAKYQFEKYVRDYTGGSLSEDNGVDFNK
NTALDKNYLLNNKIPSNNVEEAGSKNYVHYIIQLQGDDISYEATCNLFSKNPKNSIIIQRNMNESAKSY
```

| SEQ ID NOs |
|---|
| FLSDDGESILELNKYRIPERLKNKEKVKVTFIGHGKDEFNTSEFARLSVDSLSNEISSFLDTIKLDISP
KNVEVNLLGCNMFSYDFNVEETYPGKLLLSIMDKITSTLPDVNKSNITIGANQYEVRINSEGRKELLAH
SGKWINKEEAIMSDLSSKEYIFFDSIDNKLKAKSKNIPGLASISEDIKTLLLDASVSPDTKFILNNLKL
NIESSIGDYIYYEKLEPVKNIIHNSIDDLIDEFNLLENVSDELYELKKLNNLDEKYLISFEDISKNNST
YSVRFINKSNGESVYVETEKEIFSKYSEHITKEISTIKNSIITDVNGNLLDNIQLDHTSQVNTLNAAFF
IQSLIDYSSNKDVLNDLSTSVKVQLYAQLFSTGLNTIYDSIQLVNLINSNAVNDTINVLPTITEGIPVS
TILDGINLGAAIKELLDEHDPLLKKELEAKVGVLAINMSLSIAATVASIVGIGAEVTIFLLPIAGISAG
IPSLVNNELILHDKATSVVNYFNHLSESKKYGPLKTEDDKILVPIDDLVISEIDFNNNSIKLGTCNILA
MEGGSGHTVTGNIDHFFSSPSISSHIPSLSIYSAIGIETENLDFSKKIMMLPNAPSRVFWWETGAVPGL
RSLENDGTRLLDSIRDLYPGKFYWRFYAFFDYAITTLKPVYEDTNIKIKLDKDTRNFIMPTITTNEIRN
KLSYSFDGAGGTYSLLLSSYPISTNINLSKDDLWIFNIDNEVREISIENGTIKKGKLIKDVLSKIDINK
NKLIIGNQTIDFSGDIDNKDRYIFLTCELDDKISLIIEINLVAKSYSLLLSGDKNYLISNLSNTIEKIN
TLGLDSKNIAYNYTDESNNKYFGAISKTSQKSIIHYKKDSKNILEFYNDSTLEFNSKDFIAEDINVFMK
DDINTITGKYYVDNNTDKSIDFSISLVSKNQVKVNGLYLNESVYSSYLDFVKNSDGHHNTSNFMNLFLD
NISFWKLFGFENINFVIDKYFTLVGKTNLGYVEFICDNNKNIDIYFGEWKTSSSKSTIFSGNGRNVVVE
PIYNPDTGEDISTSLDFSYEPLYGIDRYINKVLIAPDLYTSLININTNYYSNEYYPEIIVLNPNTFHKK
VNINLDSSSFEYKWSTEGSDFILVRYLEESNKKILQKIRIKGILSNTQSFNKMSIDFKDIKKLSLGYIM
SNFKSFNSENELDRDHLGFKIIDNKTYYYDEDSKLVKGLININNSLFYFDPIEFNLVTGWQTINGKKYY
FDINTGAALTSYKIINGKHFYFNNDGVMQLGVFKGPDGFEYFAPANTQNNNIEGQAIVYQSKFLTLNGK
KYYFDNNSKAVTGWRIINNEKYYFNPNNAIAAVGLQVIDNNKYYFNPDTAIISKGWQTVNGSRYYFDTD
TAIAFNGYKTIDGKHFYFDSDCVVKIGVFSTNGFEYFAPANTYNNNIEGQAIVYQSKFLTLNGKKYYF
DNNSKAVTGLQTIDSKKYYFNTNTAEAATGWQTIDGKKYYFNTNTAEAATGWQTIDGKKYYFNTNTAIA
STGYTIINGKHFYFNTDGIMQIGVFKGPNGFEYFAPANTDANNIEGQAILYQNEFLTLNGKKYYFGSDS
KAVTGWRIINNKKYYFNPNNAIAAIHLCTINNDKYYFSYDGILQNGYITIERNNFYFDANNESKMVTGV
FKGPNGFEYFAPANTHNNNIEGQAIVYQNKFLTLNGKKYYFDNDSKAVTGWQTIDGKKYYFNLNTAEAA
TGWQTIDGKKYYFNLNTAEAATGWQTIDGKKYYFNTNTFIASTGYTSINGKHFYFNTDGIMQIGVFKGP
NGFEYFAPANTDANNIEGQAILYQNKFLTLNGKKYYFGSDSKAVTGWQTIDGKKYYFNTNTAVAVTGWQ
TINGKKYYFNTNTSIASTGYTIISGKHFYFNTDGIMQIGVFKGPDGFEYFAPANTDANNIEGQAIRYQN
RFLYLHDNIYYFGNNSKAATGWVTIDGNRYYFEPNTAMGANGYKTIDNKNFYFRNGLPQIGVFKGSNGF
EYFAPANTDANNIEGQAIRYQNRFLHLLGKIYYFGNNSKAVTGWQTINGKVYYFMPDTAMAAAGGLFEI
DGVIYFFGVDGVKAPGIYG |

2. Protein Sequence of *C. difficile* Toxin B - Toxinotype 0

MSLVNRKQLEKMANVRFRTQEDEYVAILDALEEYHNMSENTVVEKYLKLKDINSLTDIYIDTYKKSGRN
KALKKFKEYLVTEVLELKNNNLTPVEKNLHFVWIGGQINDTAINYINQWKDVNSDYNVNVFYDSNAFLI
NTLKKTVVESAINDTLESFRENLNDPRFDYNKFFRKRMEIIYDKQKNFINYYKAQREENPELIIDDIVK
TYLSNEYSKEIDELNTYIEESLNKITQNSGNDVRNFEEFKNGESFNLYEQELVERWNLAAASDILRISA
LKEIGGMYLDVDMLPGIQPDLFESIEKPSSVTVDFWEMTKLEAIMKYKEYIPEYTSEHFDMLDEEVQSS
FESVLASKSDKSEIFSSLGDMEASPLEVKIAFNSKGIINQGLISVKDSYCSNLIVKQIENRYKILNNSL
NPAISEDNDFNTTTNTFIDSIMAEANADNGRFMMELGKYLRVGFFPDVKTTINLSGPEAYAAAYQDLLM
FKEGSMNIHLIEADLRNFEISKTNISQSTEQEMASLWSFDDARAKAQFEEYKRNYFEGSLGEDDNLDFS
QNIVVDKEYLLEKISSLARSSERGYIHYIVQLQGDKISYEAACNLFAKTPYDSVLFQKNIEDSEIAYYY
NPGDGEIQEIDKYKIPSIISDRPKIKLTFIGHGKDEFNTDIFAGFDVDSLSTEIEAAIDLAKEDISPKS
IEINLLGCNMFSYSINVEETYPGKLLLKVKDKISELMPSISQDSIIVSANQYEVRINSEGRRELLDHSG
EWINKEESIIKDISSKEYISFNPKENKITVKSKNLPELSTLLQEIRNNSNSSDIELEEKVMLTECEINV
ISNIDTQIVEERIEEAKNLTSDSINYIKDEFKLIESISDALCDLKQQNELEDSHFISFEDISETDEGFS
IRFINKETGESIFVETEKTIFSEYANHITEEISKIKGTIFDTVNGKLVKKVNLDTTHEVNTLNAAFFIQ
SLIEYNSSKESLNLSVAMKVQVYAQLFSTGLNTITDAAKVVELVSTALDETIDLLPTLSEGLPIIATI
IDGVSLGAAIKELSETSDPLLRQEIEAKIGIMAVNLTTATTAIITSSLGIASGFSILLVPLAGISAGIP
SLVNNELVLRDKATKVVDYFKHVSLVETEGVFTLLDDKIMMPQDDLVISEIDFNNNSIVLGKCEIWRME
GGSGHTVTDDIDHFFSAPSITYREPHLSIYDVLEVQKEELDLSKDLMVLPNAPNRVFAWETGWTPGLRS
LENDGTRLLDRIRDNYEGEFYWRYFAFIADALITTLKPRYEDTNIRILLDSNTRSFIVPIITTEYIREK
LSYSFYGSGGTYALSLSQYNMGINIELSESDVWIIDVDNVVRDVTIESDKIKKGDLIEGILSTLSIEEN
KIILNSHEINFSGEVNGSNGFVSLTFSILEGINAIIEVDLLSKSYKLLISGELKILMLNSNHIQQKIDY
IGFNSELQKNIPYSFVDSEGKENGFINGSTKEGLFVSELPDVVLISKVYMDDSKPSFGYYSNNLKDVKV
ITKDNVNILTGYYLKDDIKISLSLTLQDEKTIKLNSVHLDESGVAEILKFMNRKGNTNTSDSLMSFLES
MNIKSIFVNFLQSNIKFILDANFIISGTTSIGQFEFICDENDNIQPYFIKFNTLETNYTLYVGNRQNMI
VEPNYDLDDSGDISSTVINFSQKYLYGIDSCVNKVVISPNIYTDEINITPVYETNNTYPEVIVLDANYI
NEKINVNINDLSIRYVWSNDGNDFILMSTSEENKVSQVKIRFVNVFKDKTLANKLSFNFSDKQDVPVSE
IILSFTPSYYEDGLIGYDLGLVSLYNEKFYINNFGMMVSGLIYINDSLYYFKPPVNNLITGFVTVGDDK
YYFNPINGGAASIGETIIDDKNYYFNQSGVLQTGVFSTEDGFKYFAPANTLDENLEGEAIDFTGKLIID
ENIYYFDDNYRGAVEWKELDGEMHYFSPETGKAFKGLNQIGDYKYYFNSDGVMQKGFVSINDNKHYFDD
SGVMKVGYTEIDGKHFYFAENGEMQIGVFNTEDGFKYFAHHNEDLGNEEGEEISYSGILNFNNKIYYFD
DSFTAVVGWKDLEDGSKYYFDEDTAEAYIGLSLINDGQYYFNDDGIMQVGFVTINDKVFYFSDSGIIES
GVQNIDDNYFYIDDNGIVQIGVFDTSDGVKYFAPANTVNDNIYGQAVEYSGILNFRVGEDVYYFGETYTIE
TGWIYDMENESDKYYFNPETKKACKGINLIDDIKYYFDEKGIMRTGLISFENNYYFNENGEMQFGYIN
IEDKMFYFGEDGVMQIGVFNTPDGFKYFAHQNTLDENFEGESINYTGWLDLDEKRYYFTDEYIAATGSV
IIDGEEYYFDPDTAQLVISE

3. Protein Sequence of *C. difficile* Toxin A - Toxinotype III

MSLISKEELIKLAYSIRPRENEYKTILTNLDEYNKLTTNNNENKYLQLKKLNESIDVFMNKYKNSSRNR
ALSNLKKDILKEVILIKNSNTSPVEKNLHFVWIGGEVSDIALEYIKQWADINAEYNIKLWYDSEAFLVN
TLKKAIVESSTTEALQLLEEEIQNPQDNMKFYKKRMEFIYDRQKRFINYYKSQINKPTVPTIDDIIKS
HLVSEYNRDETLLESYRTNSLRKINSNHGIDIRANSLFTEQELLNIYSQELLNRGNLAAASDIVRLLAL
KNFGGVYLDVDMLPGIHSDLFKTIPRPSSIGLDRWEMIKLEAIMKYKKYINNYTSENFDKLDQQLKDNF
KLIIESKSEKSEIFSKLENLNVSDLEIKIAFALGSVINQALISKQGSYLTNLVIEQVKNRYQFLNQHLN
PAIESDNNFTDTTKIFHDSLFNSATAENSMFLTKIAPYLQVGFMPEARSTISLSGPGAYASAYYDFINL
QENTIEKTLKASDLIEFKFPENNLSQLTEQEINSLWSFDQASAKYQFEKYVRDYTGGSLSEDNGVDFNK

| SEQ ID NOs |
| --- |
| NTALDKNYLLNNKIPSNNVEEAGSKNYVHYIIQLQGDDISYEATCNLFSKNPKNSIIIQRNMNESAKSY
FLSDDGESILELNKYRIPERLKNKEKVKVTFIGHGKDEFNTSEFARLSVDSLSNEISSFLDTIKLDISP
KNVEVNLLGCNMFSYDFNVEETYPGKLLLSIMDKITSTLPDVNKDSITIGANQYEVRINSEGRKELLAH
SGKWINKEEAIMSDLSSKEYIFFDSIDNKLKAKSKNIPGLASISEDIKTLLLDASVSPDTKFILNNLKL
NIESSIGDYIYYEKLEPVKNIIHNSIDDLIDEFNLLENVSDELYELKKLNNLDEKYLISFEDISKNNST
YSVRFINKSNGESVYVETEKEIFSKYSEHITKEISTIKNSITDVNGNLLDNIQLDHTSQVNTLNAAFF
IQSLIDYSSNKDVLNDLSTSVKVQLYAQLFSTGLNTIYDSIQLVNLISNAVNDTINVLPTITEGIPIVS
TILDGINLGAAIKELLDEHDPLLKKELEAKVGVLAINMSLSIAATVASIVGIGAEVTIFLLPIAGISAG
IPSLVNNELILHDKATSVVNYFNHLSESKEYGPLKTEDDKILVPIDDLVISEIDFNNNSIKLGTCNILA
MEGGSGHTVTGNIDHFFSSPYISSHIPSLSVYSAIGIKTENLDFSKKIMMLPNAPSRVFWWETGAVPGL
RSLENNGTKLLDSIRDLYPGKFYWRFYAFFDYAITTLKPVYEDTNTKIKLDKDTRNFIMPTITTDEIRN
KLSYSFDGAGGTYSLLLSSYPISMNINLSKDDLWIFNIDNEVREISIENGTIKKGNLIEDVLSKIDINK
NKLIIGNQTIDFSGDIDNKDRYIFLTCELDDKISLIIEINLVAKSYSLLLSGDKNYLISNLSNTIEKIN
TLGLDSKNIAYNYTDESNNKYFGAISKTSQKSIIHYKKDSKNILEFYNGSTLEFNSKDFIAEDINVFMK
DDINTITGKYYVDNNTDKSIDFSISLVSKNQVKVNGLYLNESVYSSYLDFVKNSDGHHNTSNFMNLFLN
NISFWKLFGFENINFVIDKYFTLVGKTNLGYVEFICDNNKNIDIYFGEWKTSSSKSTIFSGNGRNVVVE
PIYNPDTGEDISTSLDFSYEPLYGIDRYINKVLIAPDLYTSLININTNYYSNEYYPEIIVLNPNTFHKK
VNINLDSSSFEYKWSTEGSDFILVRYLEESNKKILQKIRIKGILSNTQSFNKMSIDFKDIKKLSLGYIM
SNFKSFNSENELDRDHLGFKIIDNKTYYDEDSKLVKGLININNSLFYFDPIESNLVTGWQTINGKKYY
FDINTGAASTSYKIIINGKHFYFNNNGVMQLGVFKGPDGFEYFAPANTQNNNIEGQAIVYQSKFLTLNGK
KYYFDNDSKAVTGWRIINNEKYYFNPNNAIAAVGLQVIDNNKYYFNPDTAIISKGWQTVNGSRYYFDTD
TAIAFNGYKTIDGKHFYFDSDCVVKIGVFSGSNGFEYFAPANTYNNNIEGQAIVYQSKFLTLNGKKYYF
DNNSKAVTGWQTIDSKKYYFNTNTAEAATGWQTIDGKKYYFNTNTAEAATGWQTIDGKKYYFNTNTSIA
STGYTIINGKYFYFNTDGIMQIGVFKVPNGFEYFAPANTHNNNIEGQAILYQNKFLTLNGKKYYFGSDS
KAITGWQTIDGKKYYFNPNNAIAATHLCTINNDKYYFSYDGILQNGYITIERNNFYPDANNESKMVTGV
FKGPNGFEYFAPANTHNNNIEGQAIVYQNKFLTLNGKKYYFDNDSKAVTGWQTIDSKKYYFNLNTAVAV
TGWQTIDGEKYFYNLNTAEAATGWQTIDGKRYYFNTNTYIASTGYTIINGKHFYFNTDGIMQIGVFKGP
DGFEYFAPANTHNNNIEGQAILYQNKFLTLNGKKYYFGSDSKAVTGLRTIDGKKYYFNTNTAVAVTGWQ
TINGKKYYFNTNTYIASTGYTIISGKHFYFNTDGIMQIGVFKGPDGFEYFAPANTDANNIEGQAIRYQN
RFLYLHDNIYYFGNDSKAATGWATIDGNRYYFEPNTAMGANGYKTIDNKNFYFRNGLPQIGVFKGPNGF
EYFAPANTDANNIDGQAIRYQNRFLHLLGKIYYFGNNSKAVTGWQTINSKVYYFMPDTAMAAAGGLFEI
DGVIYFFGVDGVKAPGIYG |

4. Protein Sequence of *C. difficile* Toxin B - Toxinotype III
MSLVNRKQLEKMANVRFRVQEDEYVAILDALEEYHNMSENTVVEKYLKLKDINSLTDTIYIDTYKKSGRN
KALKKFKEYLVTEVLELKNNNLTPVEKNLHFVWIGGQINDTAINYINQWKDVNSDYNVNVFYDSNAFLI
NTLKKTIVESATNDTLESFRENLNDPRFDYNKFYRKRMEIIYDKQKNFINYYKTQREENPDLIIDDIVK
IYLSNEYSKDIDELNSYIEESLNKVTENSGNDVRNFEEFKGGESFKLYEQELVERWNLAAASDILRISA
LKEVGGVYLDVDMLPGIQPDLFESIEKPSSVTVDFWEMVKLEAIMKYKEYIPGYTSEHFDMLDEEVQSS
FESVLASKSDKSEIFSSLGDMEASPLEVKIAFNSKGIINQGLISVKTDYCSNLIVKQIENRYKILNNSL
NPAISEDNDFNTTTNAFIDSIMAEANADNGRFMMELGKYLRVGFFPDVKTTINLSGPEAYAAAYQDLLM
FKEGSMNIHLIEADLRNFEISKTNISQSTEQEMASLWSFDDARAKAQFEEYKKNYFEGSLGEDDNLDFS
QNTVVDKEYLLEKISSLARSSERGYIHYIVQLQGDKISYEAACNLFAKTPYDSVLFQKNIEDSEIAYY
NPGDGEIQEIDKYKIPSIISDRPKIKLTFIGHGKDEFNTDIFAGLDVDSLSTEIETAIDLAKEDISPKS
IEINLLGCNMFSYSVNVEETYPGKLLLRVKDKVSELMPSISQDSIIVSANQYEVRINSEGRRELLDHSG
EWINKEESIIKDISSKEYISFNPKENKIIVKSKNLPELSTLLQEIRNNSNSSDIELEEKVMLAECEINV
ISNIDTQVVEGRIEEAKSLTSDSINYIKNEFKLIESISDALYDLKQQNELEESHFISFEDILETDEGFS
IRFIDKETGESIFVETEKAIFSEYANHITEEISKIKGTIFDTVNGKLVKKVNLDATHEVNTLNAAFFIQ
SLIEYNSSKESLSNLSVAMKVQVYAQLFSTGLNTITDAAKVVELVSTALDETIDLLPTLSEGLPVIATI
IDGVSLGAAIKELSETSDPLLRQEIEAKIGIMAVNLTAATTAIITSSLGIASGFSILLVPLAGISAGIP
SLVNNELILRDKATKVVDYFSHISLAESEGAFTSLDDKIMMPQDDLVISEIDFNNNSITLGKCEIWRME
GGSGHTVTDDIDHFFSAPSITYREPHLSIYDVLEVQKEELDLSKDLMVLPNAPNRVFAWETGWTPGLRS
LENDGTKLLDRIRDNYEGEFYWRYFAFIADALITTLKPRYEDTNIRINLDSNTRSFIVPVITTEYIREK
LSYSFYGSGGTYALSLSQYNMNINIELNENDTWVIDVDNVVRDVTIESDKIKKGDLIENILSKLSIEDN
KIILDNHEINFSGTLNGGNGFVSLTFSILEGINAVIEVDLLSKSYKVLISGELKTLMANSNSVQQKIDY
IGLNSELQKNIPYSFMDDKGKENGFINCSTKEGLFVSELSDVVLISNKSKPLFGYCSNDLKDVKV
ITKDDVIILTGYYLKDDIKISLSFTIQDENTIKLNGVYLDENGVAEILKFMNKKGSTNTSDSLMSFLES
MNIKSIFINSLQSNTKLILDTNFIISGTTSIGQFEFICDKDNNIQPYFIKFNTLETKYTLYVGNRQNMI
VEPNYDLDDSGDISSTVINFSQKYLYGIDSCVNKVIISPNIYTDEINITPIYEANNTYPEVIVLDTNYI
SEKININNDLSIRYVWSNDGSDFILMSTDEENKVSQVKIRFTNVFKGNTISDKISFNFSDKQDVSINK
VISTFTPSYYVEGLLNYDLGLISLYNEKFYINNFGMMVSGLVYINDSLYFKPPIKNLITGFTTIGDDK
YYFNPDNGGAASVGETIIDGKNYYFSQNGVLQTGVFSTEDGFKYFAPADTLDENLEGEAIDFTGKLTID
ENVYYFGDNYRAAIEWQTLDDEVYYFSTDTGRAFKGLNQIGDDKFYFNSDGIMQKGFVNINDKTFYFDD
SGVMKSGYTEIDGKYFYFAENGEMQIGVFNTADGFKYFAHHDEDLGNEEGEALSYSGILNFNNKIYYFD
DSFTAVVGWKDLEDGSKYYFDEDTAEAYIGISIINDGKYYFNDSGIMQIGFVTINNEVFYFSDSGIVES
GMQNIDDNYFYIDENGLVQIGVFDTSDGYKYFAPANTVNDNIYGQAVEYSGLVRVGEDVYYFGETYTIE
TGWIYDMENESDKYYFDPETKKAYKGINVIDDIKYYFDENGIMRTGLITFEDNHYYFNEDGIMQYGYLN
IEDKTFYFSEDGIMQIGVFNTPDGFKYFAHQNTLDENFEGESINYTGWLDLDEKRYYFTDEYIAATGSV
IIDGEEYYFDPDTAQLVISE 5. Protein Sequence of *C. difficile* Binary toxin fragment A
MKKFRKHKRISNCISILLILYLTLGGLLPNNIYAQDLQSYSEKVCNTTYKAPIESFLKDKEKAKEWERK
EAERIEQKLERSEKEALESYKKDSVEISKYSQTRNYFDYQIEANSREKEYKELRNAISKNKIDKPMYV
YYFESPEKFAFNKVIRTENQNEISLEKFNEFKETIQNKLFKQDGFKDISLYEPGKGDEKPTPLLMHLKL
PRNTGMLPYTNTNNVSTLIEQGYSIKIDKIVRIVIDGKHYIKAEASVVNSLDFKDDVSKGDSWGKANYN
DWSNKLTPNELADVNDYMRGGYTAINNYLISNGPVNNPNPELDSKITNIENALKREPIPTNLTVYRRSG
PQEFGLTLTSPEYDFNKLENIDAFKSKWEGQALSYPNFISTSIGSVNMSAFAKRKIVLRITIPKGSPGA
YLSAIPGYAGEYEVLLNHGSKFKINKIDSYKDGTITKLIVDATLIP

SEQ ID NOs

6. Protein Sequence of *C. difficile* Binary toxin fragment B

MKIQMRNKKVLSFLTLTAIVSQALVYPVYAQTSTSNHSNKKKEIVNEDILPNNGLMGYYFSDEHFKDLK
LMAPIKDGNLKFEEKKVDKLLDKDKSDVKSIRWTGRIIPSKDGEYTLSTDRDDVLMQVNTESTISNTLK
VNMKKGKEYKVRIELQDKNLGSIDNLSSPNLYWELDGMKKIIPEENLFLRDYSNIEKDDPFIPNNNFFD
PKLMSDWEDEDLDTDNDNIPDSYERNGYTIKDLIAVKWEDSFAEQGYKKYVSNYLESNTAGDPYTDYEK
ASGSFDKAIKTEARDPLVAAYPIVGVGMEKLIISTNEHASTDQGKTVSRATTNSKTESNTAGVSVNVGY
QNGFTANVTTNYSHTTDNSTAVQDSNGESWNTGLSINKGESAYINANVRYYNTGTAPMYKVTPTTNLVL
DGDTLSTIKAQENQIGNNLSPGDTYPKKGLSPLALNTMDQFSSRLIPINYDQLKKLDAGKQIKLETTQV
SGNFGTKNSSGQIVTEGNSWSDYISQIDSISASIILDTENESYERRVTAKNLQDPEDKTPELTIGEAIE
KAFGATKKDGLLYFNDIPIDESCVELIFDDNTANKIKDSLKTLSDKKIYNVKLERGMNILIKTPTYFTN
FDDYNNYPSTWSNVNTTNQDGLQGSANKLNGETKIKIPMSELKPYKRYVFSGYSKDPLTSNSIIVKIKA
KEEKTDYLVPEQGYTKFSYEFETTEKDSSNIEITLIGSGTTYLDNLSITELNSTPEILDEPEVKIPTDQ
EIMDAHKIYFADLNFNPSTGNTYINGMYFAPTQTNKEALDYIQKYRVEATLQYSGFKDIGTKDKEMRNY
LGDPNQPKTNYVNLRSYFTGGENIMTYKKLRIYAITPDDRELLVLSVD

The invention claimed is:

1. A method for treatment of *Clostridium difficile* infection, said method comprising administering a pharmaceutical composition, comprising:
   ovine antibodies that bind to *C. difficile* Toxin A,
   ovine antibodies that bind to *C. difficile* Toxin B, and
   at least one component selected from the group consisting of a pharmaceutically acceptable carrier, excipient and salt for parenteral administration.

2. The method according to claim 1, wherein the antibodies are polyclonal antibodies.

3. The method according to claim 1, wherein the *C. difficile* Toxin A is selected from the group consisting of: Toxinotype 0, Toxinotype III and Toxinotype V.

4. The method according to claim 1, wherein the *C. difficile* Toxin B is selected from the group consisting of: Toxinotype 0, Toxinotype III and Toxinotype V.

5. The method according to claim 1, wherein the pharmaceutical composition further comprises ovine antibodies that bind to *C. difficile* Binary Toxin.

6. The method according to claim 5, wherein the antibodies are polyclonal antibodies.

* * * * *

UNITED STATES PATENT AND TRADEMARK OFFICE
CERTIFICATE OF CORRECTION

PATENT NO.         : 8,709,428 B2
APPLICATION NO.    : 13/202557
DATED              : April 29, 2014
INVENTOR(S)        : Clifford Shone et al.

Page 1 of 1

It is certified that error appears in the above-identified patent and that said Letters Patent is hereby corrected as shown below:

Title Page:

Item (73) Assignee:

Please delete "Health Protection Agency, Salisbury (GB)" and insert --The Secretary of State for Health, London (GB)--

Page 2. Item (56) References Cited:

Col. 1, Line 30, please delete "*ficule*"" and insert --*ficile*"--
Col. 1, Line 55, please delete "}"
Col. 1, Line 66, please delete "hiswtiding" and insert --histidine--

Col. 2, Line 67, please delete "/polycional_" and insert --/polyclonal_--

Signed and Sealed this
Twenty-ninth Day of March, 2016

Michelle K. Lee
*Director of the United States Patent and Trademark Office*